US012637490B2

(12) United States Patent
Lauceri et al.

(10) Patent No.: US 12,637,490 B2
(45) Date of Patent: May 26, 2026

(54) METHOD FOR THE EXTRACTION OF PHYCOBILIPROTEINS AT HIGH PURITY DEGREE FROM CYANOBACTERIAL AND/OR ALGAL BIOMASSES

(71) Applicant: Consiglio Nazionale delle Ricerche, Rome (IT)

(72) Inventors: Rosaria Lauceri, Rome (IT); Graziella Chini Zittelli, Rome (IT); Giuseppe Torzillo, Rome (IT)

(73) Assignee: Consiglio Nazionale delle Ricerche, Rome (IT)

( * ) Notice: Subject to any disclaimer, the term of this patent is extended or adjusted under 35 U.S.C. 154(b) by 371 days.

(21) Appl. No.: 18/258,225

(22) PCT Filed: Dec. 22, 2021

(86) PCT No.: PCT/IB2021/062187
§ 371 (c)(1),
(2) Date: Jun. 19, 2023

(87) PCT Pub. No.: WO2022/144704
PCT Pub. Date: Jul. 7, 2022

(65) Prior Publication Data
US 2024/0101596 A1 Mar. 28, 2024

(30) Foreign Application Priority Data
Dec. 29, 2020 (IT) ........................ 102020000032636

(51) Int. Cl.
*C07K 1/14* (2006.01)
*C07K 14/195* (2006.01)
*C07K 14/405* (2006.01)

(52) U.S. Cl.
CPC ............ *C07K 1/145* (2013.01); *C07K 14/195* (2013.01); *C07K 14/405* (2013.01)

(58) Field of Classification Search
None
See application file for complete search history.

(56) References Cited

FOREIGN PATENT DOCUMENTS

| CN | 102993297 | * | 4/2014 |
| CN | 106939043 | * | 7/2017 |
| JP | 2004 027041 A | | 1/2004 |
| WO | WO 2019/234614 A2 | | 12/2019 |

OTHER PUBLICATIONS

International search report and written opinion dated May 30, 2022; Application No. PCT/IB2021/062187; 11 pages.
Lauceri Rosaria et al: "A simple method for rapid purification of phycobiliproteins from Arthrospira platensis and Porphyridium cruentum biomass", Algal Research, vol. 44, Dec. 1, 2019 (Dec. 1, 2019); 11 pages.

* cited by examiner

*Primary Examiner* — Susan Hoffman
(74) *Attorney, Agent, or Firm* — Rankin Hill & Clark, LLP; Erik J. Overberger

(57) ABSTRACT

The object of the invention is a method for extracting, with high yield, phycobiliproteins from cyanobacterial and/or algal biomass, obtaining extracts in water or aqueous solutions characterised by high pigment concentration and a purity degree equal to or greater than the food/cosmetic grade (P≥2). The method is based on a process characterised by a step of breaking down the cyanobacterial/algal cells by ultrasonication in an aqueous solution of ammonium sulphate, and simultaneous extraction of water-soluble compounds other than phycobiliproteins, followed by an extraction step of the phycobiliproteins using water or aqueous solutions.

14 Claims, 13 Drawing Sheets

---- Spirulina sample: Not diluted waste solution 1 (AS 1.1 M)

—— Spirulina sample: Phycobiliprotein extract in CaCl₂ 0.05 M, diluted 16 times

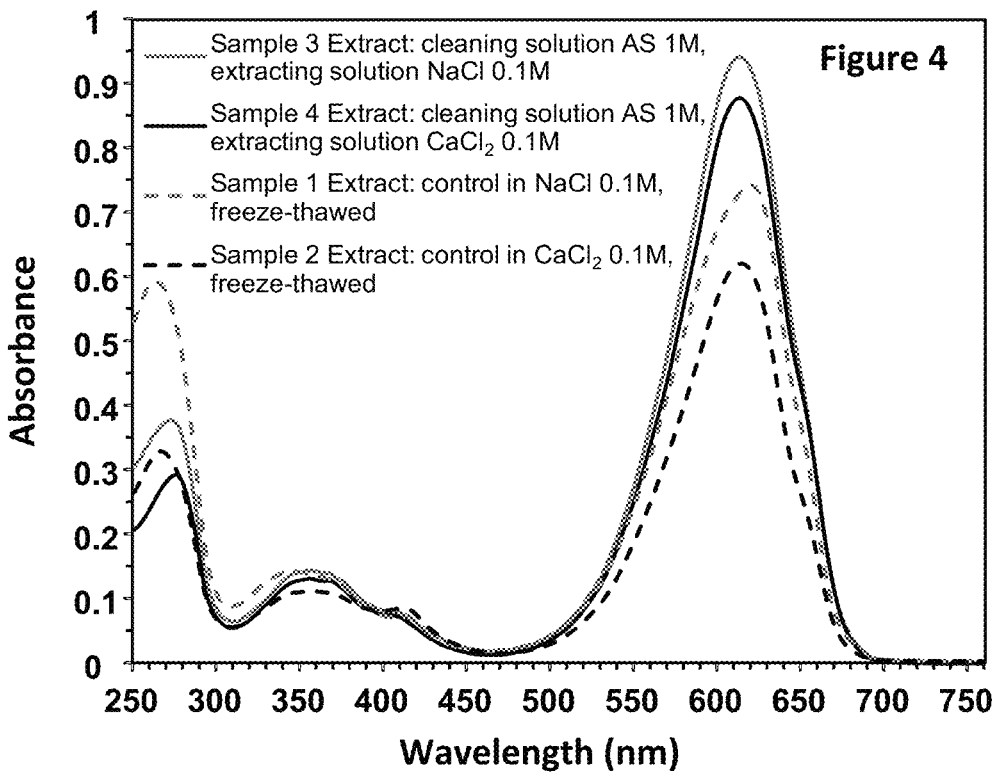
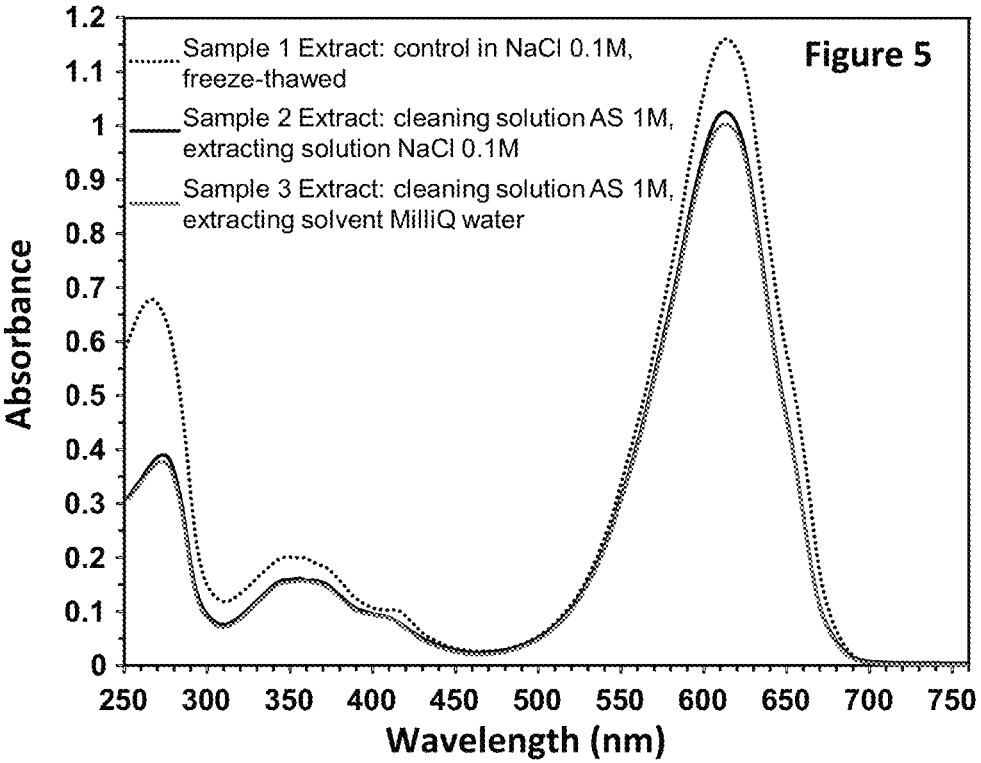

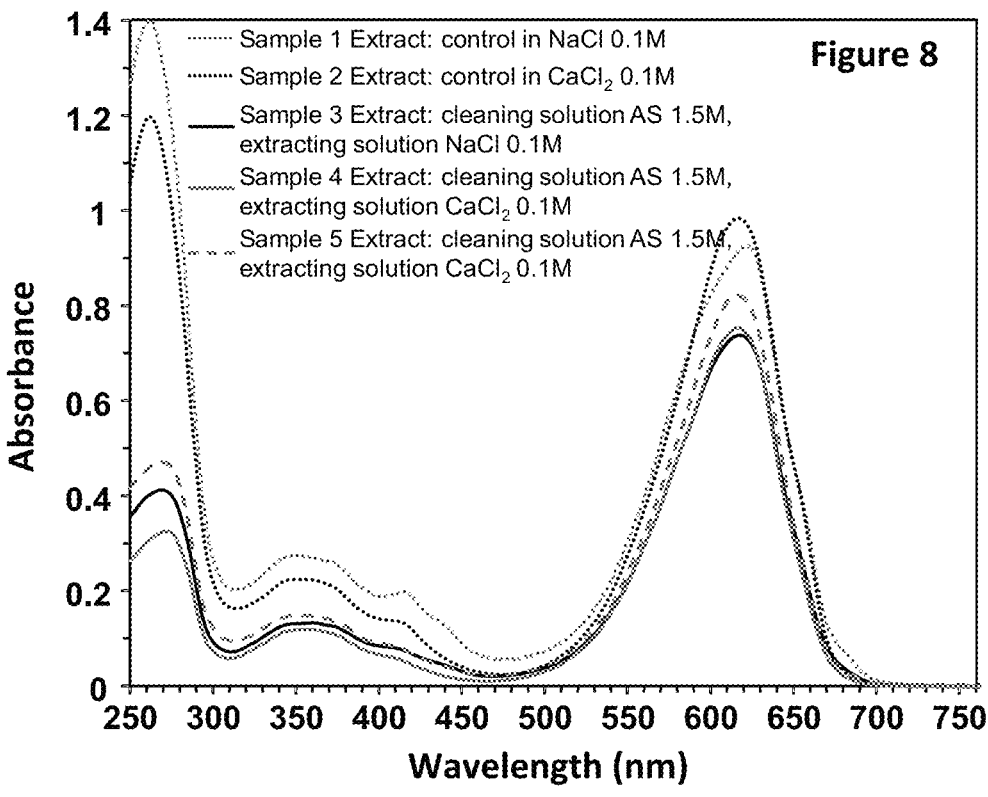

Figure 8

Sample 1 Extract: control in NaCl 0.1M
Sample 2 Extract: control in CaCl$_2$ 0.1M
Sample 3 Extract: cleaning solution AS 1.5M, extracting solution NaCl 0.1M
Sample 4 Extract: cleaning solution AS 1.5M, extracting solution CaCl$_2$ 0.1M
Sample 5 Extract: cleaning solution AS 1.5M, extracting solution CaCl$_2$ 0.1M

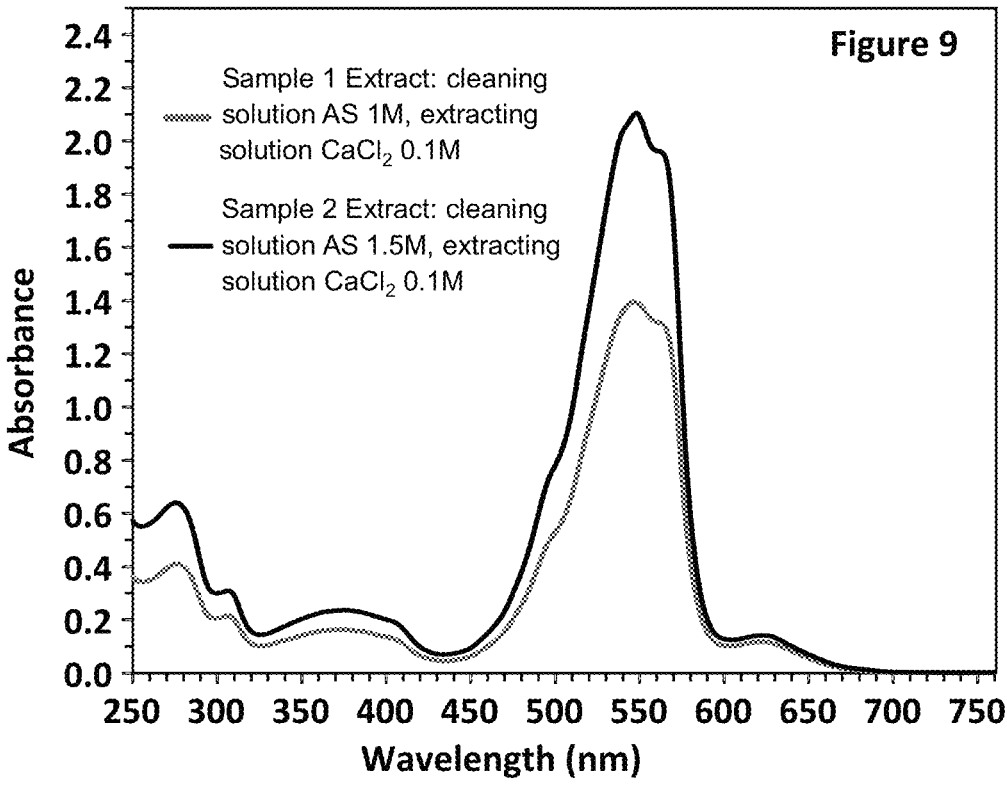

Figure 9

Sample 1 Extract: cleaning solution AS 1M, extracting solution CaCl$_2$ 0.1M

Sample 2 Extract: cleaning solution AS 1.5M, extracting solution CaCl$_2$ 0.1M

Legend:
- 1 Not diluted Extract. Sonic cycles: 2
- 2 Not diluted Extract. Sonic cycles: 2
- 3 0.2 mL Estr + 3 mL CaCl2 0.05 M. Sonic cycles: 2
- 4 0.2 mL Estr + 3 mL CaCl2 0.05 M. Sonic cycles: 2
- 5 0.2 mL Estr + 3 mL CaCl2 0.05 M. Sonic cycles: 3
- 6 0.2 mL Estr + 3 mL CaCl2 0.05 M. Sonic cycles: 3
- 7 0.2 mL Estr + 3 mL CaCl2 0.05 M. Sonic cycles: 4
- 8 0.2 mL Estr + 3 mL CaCl2 0.05 M. Sonic cycles: 4

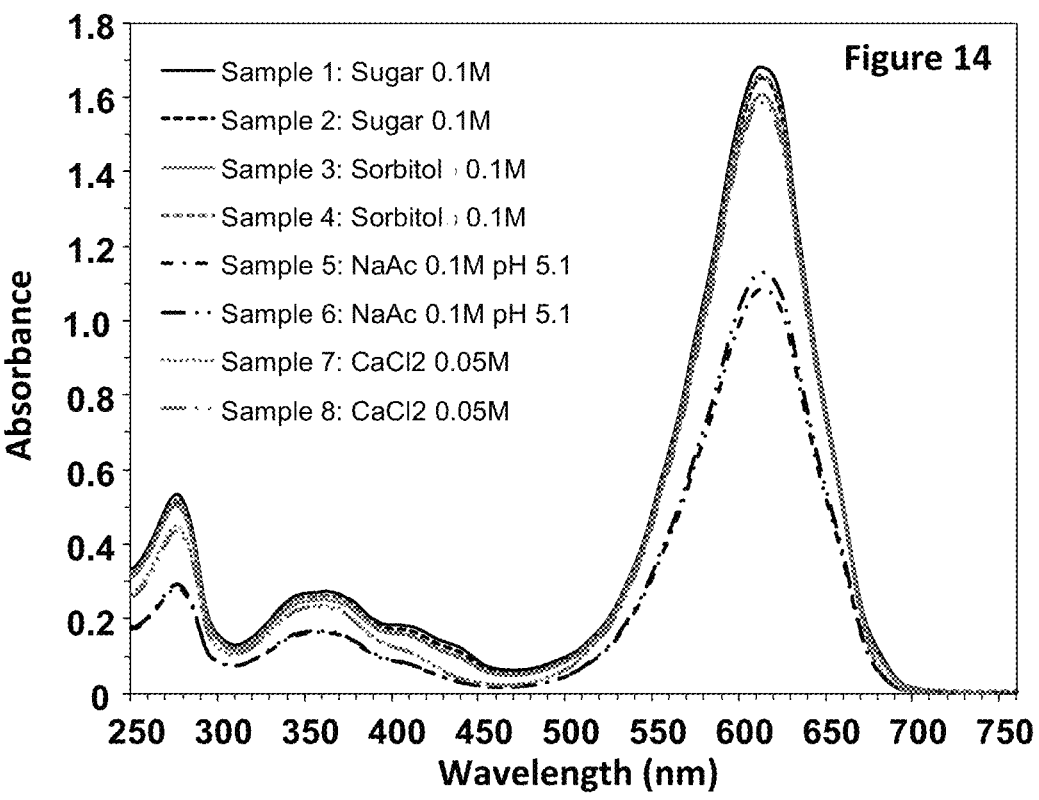
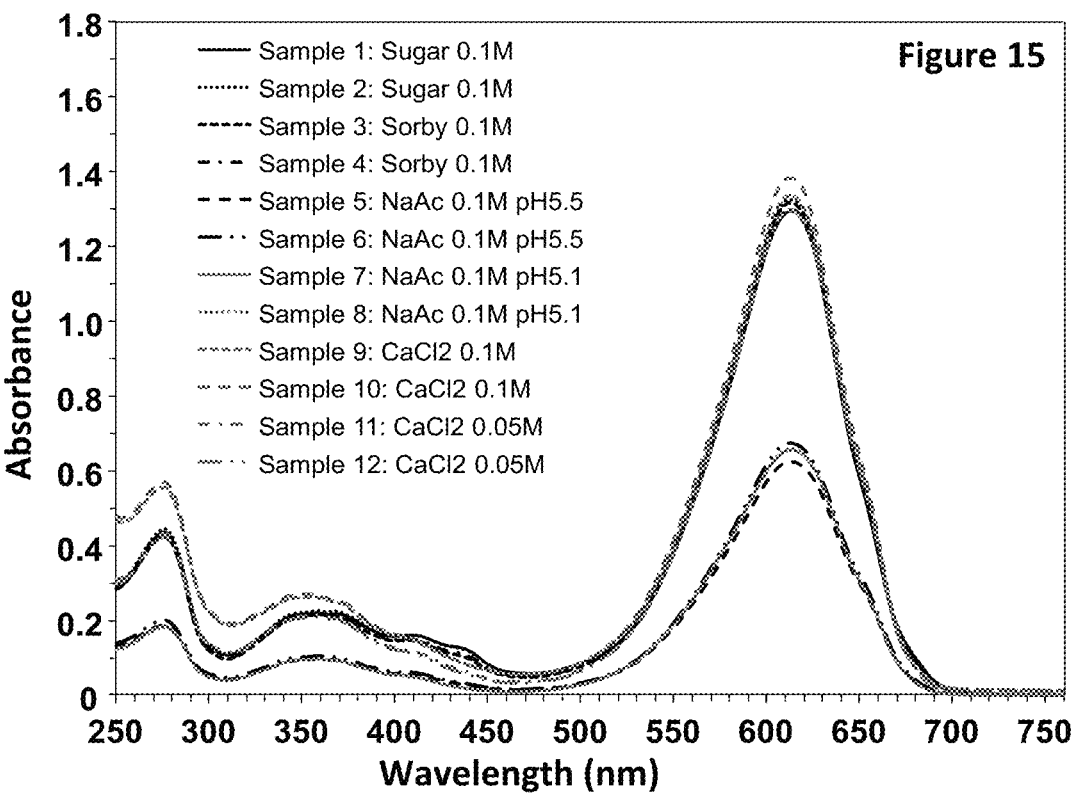

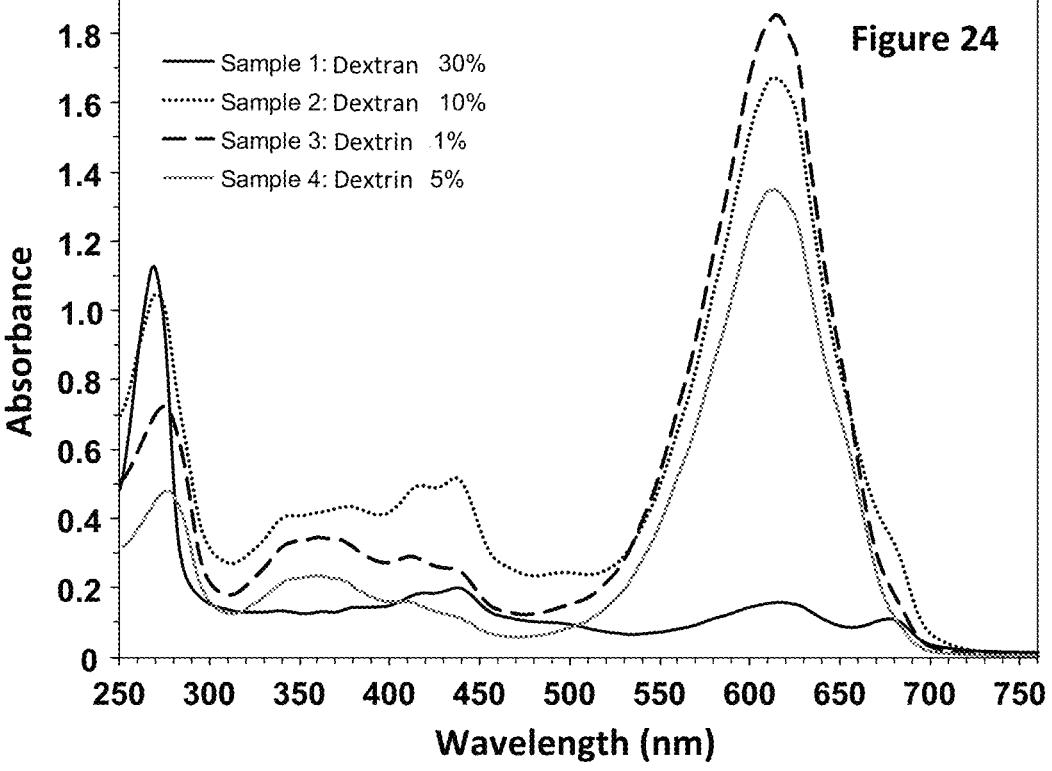

METHOD FOR THE EXTRACTION OF PHYCOBILIPROTEINS AT HIGH PURITY DEGREE FROM CYANOBACTERIAL AND/OR ALGAL BIOMASSES

FIELD OF THE INVENTION

The present invention falls within the field of methods of extraction and purification of active ingredients from natural substrates for cosmetic, food, nutraceutical and biomedical use; in particular, the invention relates to methods for extracting and purifying phycobiliproteins from cyanobacteria and/or algae.

BACKGROUND

Phycobiliproteins are pigments characterized by bright, highly fluorescent colours that are part of the antenna complexes of the photosynthetic system of cyanobacteria and some algae, such as the Rhodophyta and *Cryptophyta* classes.

Phycobiliproteins are formed by a complex between proteins and linear tetrapyrrole groups (chromophores) covalently linked to the protein units.

The most common phycobiliproteins are phycocyanin (PC), allophycocyanin (APC) and phycoerythrin (PE). These water-soluble, bright blue (phycocyanin and allophycocyanin) and bright fuchsia (phycoerythrin) coloured pigments are products with considerable added value, with various commercial applications.

Phycobiliproteins are used as natural cosmetic dyes or as fluorescent probes (allophycocyanin and phycoerythrin in particular); examples of practical applications are flow cytometry and immunoassays.

Phycocyanin is one of the rare natural blue dyes available in the food sector and is widely used in the food industry. Phycocyanin (aqueous extracts also containing allophycocyanin) obtained from *Arthrospira platensis* (*Spirulina*) has been approved by EFSA (Regulation (EU) No. 1333/2008 and No. 231/2012), as a food dye, and by the US FDA (21CFR73.1530), as a natural food additive/dye.

Currently, the market of natural food dyes is growing strongly worldwide and is estimated to reach $1.77 billion by 2021. In addition, various therapeutic properties of phycocyanin have been reported, such as antioxidant, anti-inflammatory, neuroprotective, anticancer and immunomodulatory activity.

The commercial value of a phycobiliprotein depends strongly on its purity degree. The purity degree of the phycobiliproteins is generally assessed using the ratio of the maximum absorbance value of each phycobiliprotein (at about 540-570 nm for phycoerythrin, at about 615-620 nm for phycocyanin, at about 650 nm for allophycocyanin) to the absorbance value at 280 nm, which is related to the total amount of protein in the product.

A product with a purity (P) greater than 0.7 is considered food grade, greater than 1.5 cosmetic grade, greater than 3.9 reactive grade (or reagent) and greater than 4.0 analytical grade. Typically, a product with a purity greater than 3.0 is required for use as a fluorescent agent, whereas an analytical grade product is required for biomedical and therapeutic applications.

The purification of the phycobiliproteins is a complex and time-consuming process; in fact, many state-of-the-art purification methods have been proposed. High purity can usually be achieved by applying several purification steps, often involving several packed-column chromatographic methods; these techniques reduce product yield and increase costs, hindering large-scale exploitation.

Several simplified chromatographic purification processes, more suitable for large-scale production of phycobiliproteins, have been proposed.

Some protocols completely avoid the costly and time-consuming purification steps of the packed-column chromatography; however, these methods have some drawbacks and do not always meet the requirements of large-scale production.

By way of example, methods known to the state of the art that do not make use of chromatographic techniques for extracting phycobiliproteins are described below:

CN106008705A describes a method for separating and purifying phycocyanin from the blue alga *Spirulina* by combining two aqueous steps of extraction and ultra-sonication. The method comprises in particular a step of extraction and a step of purifying the sample, but does not comprise any step of cleaning/purifying the sample after extraction.

The extraction according to the method described therein provides that the biomass in powder, after having been rehydrated for 6-8 hours, is submitted to cell lysis through 3-4 freeze-thawing cycles; the resulting suspension is centrifuged, the supernatant collected to obtain the raw extract of phycocyanin. The subsequent purification step is carried out using a biphasic aqueous system consisting of a polysaccharide, dextran, and an inorganic salt, such as ammonium sulphate, sodium sulphate or magnesium sulphate. These components are added to the raw extract of phycocyanin in appropriate amounts and the mixture submitted to sonication. Sonication promotes the separation of the two phases (in 15-30 minutes) without the need for centrifugation to be applied. The upper phase of the biphasic system containing the phycocyanin is recovered, dialysed (using a 5 KDa membrane) and freeze-dried, obtaining a product with a purity P=3.5-3.8 and a yield Y=90% (note that for the purpose of determining the yield, the raw extract is considered to be 100%).

CN109879943A describes a method for extracting and purifying phycoerythrin (PE) from red algae, applying a cleaning/purification process upstream of the extraction step.

The cleaning/purification step provides for pulverising a biomass containing 50-80% water so as to obtain particles of 28-150 μm in diameter. The biomass is suspended in a mixture of alcohols/ketones (e.g. ethanol/acetone) for no more than 60 minutes, and filtered to remove the solvents and the dissolved substances. The biomass is dried at T<40° C. to remove most of the organic solvents and water. This is followed by the extraction step, in which it is provided that water is added to the dried biomass, allowing it under extraction for 1-5 hours (T=0-25° C.). The suspension is filtered, centrifuged and the supernatant recovered. A raw extract of phycoerythrin is thus obtained. The process ends with a step of purifying the extract, according to which ammonium sulphate (AS) is added to the raw extract in a ratio between 5:100 and 50:100. The suspension is allowed to stabilise for 2-8 hours and is centrifuged. However, it should be noted that the salting-out process carried out with AS does not affect phycoerythrin, but contaminating proteins that require a lower concentration of AS than phycoerythrin to precipitate. The supernatant represents the purified extract of PE (P=1.5-1.3).

CN104086649A describes a method for extracting phycobiliproteins from *Spirulina*, comprising a step of extracting chlorophyll and carotenoids from the *spirulina* biomass, followed by the extraction of the phycobiliproteins. The process of extracting hydrophobic photosynthetic pigments also represents the cleaning/purification step upstream of the phycobiliprotein extraction process.

The cleaning/purification step requires that the fresh pressed biomass is treated with ethanol (at least 80% of the total volume) in order to be dehydrated and to extract chlorophyll and carotenoids. The suspension is stirred and then centrifuged. The supernatant contains chlorophyll and carotenoids, while the phycobiliproteins are contained in the precipitate (pellet), which is submitted to freeze-drying. This is followed by the extraction step, which involves suspending the freeze-dried pellet in a phosphate buffer solution, stirring the suspension for 3-5 hours at 40-50° C. The suspension is finally centrifuged, thus obtaining the extract (supernatant) of phycobiliproteins, with a rather low yield (Y %=4.3-5.5). The method does not include any final purification step.

WO2019/234614, in the name of the Applicant, describes a process for purifying phycobiliproteins from raw extracts of cyanobacteria and/or algae. In particular, the process provides that the raw extract of phycobiliproteins is submitted to at least one purification cycle on the chromatographic membrane (page 4, lines 7-10). According to an embodiment of the method, the starting raw extract can be obtained by suspending a freeze-dried *A. platensis* biomass in an aqueous solution of ammonium sulphate 0.6 M. The suspension, kept at 4° C. for 24 hours, is centrifuged; the supernatant, containing phycocyanin and allophycocyanin (constituent of the raw extract), is recovered in order to be then submitted to purification on a chromatographic membrane.

JP2004027041 describes a method for purifying phycocyanin. The method provides for subjecting a cyanobacterial biomass to sonication in the presence of a calcium or phosphate salt in order to extract the phycocyanin by bringing it into solution. A flocculating agent is added to the suspension containing the extracted phycocyanin (phosphate salt, if the extraction was carried out in the presence of calcium; calcium salt if the extraction was carried out in the presence of phosphate ion), which serves to aggregate the contaminating biomolecules other than phycocyanin (such as, for example, other colouring pigments such as chlorophyll), causing them to precipitate and thus facilitating their separation from the sample. Only after flocculation the raw extract of phycocyanin is obtained by separation from the biomass.

Problem of the Prior Art

The widespread use of PC and other phycobiliproteins has been hampered by the high cost of the large-scale extraction and, above all, purification process, which remains problematic and costly.

The extraction of phycobiliproteins from cyanobacterial cells is difficult due to the thick cell wall, which is characterised by a multi-layer structure. The extraction method must be optimised for each species and there is no standard method for quantitative extraction.

Among the various methods used for extracting phycobiliproteins, repeated freeze-thawing cycles are recognised as one of the most reliable, reproducible and robust extraction methods for many cyanobacteria (including *Spirulina*) and the best method for achieving higher purity; however, it is time-consuming and more suitable to be used for small amounts of biomass.

On the other hand, ultrasonication ensures easier operation, short times, minimal losses, low solvent consumption and high yield. Ultrasonication represents an efficient and economical option for industrial production; however, the product obtained is usually characterised by a lower purity.

This is a fairly general rule for large-scale production of phycobiliproteins: purity is generally low, especially when yield is high. In addition, sonication causes a strong contamination by chlorophyll/carotenoids, which influences the colour of the product (see FIG. 2).

Finally, it should be noted that the use of organic solvents destabilises the structure of the phycobiliproteins and may, therefore, cause a partial denaturation of the protein of interest.

Therefore, low purity and/or contamination by chlorophyll/carotenoids makes it necessary to apply a purification process downstream of the extraction in order to obtain a product of commercial interest.

SUMMARY OF THE INVENTION

The object of the invention is a method for extracting phycobiliproteins with high yield starting from cyanobacterial and/or algal biomasses, obtaining extracts in water or aqueous solutions characterised by a high concentration of pigments and a purity degree equal to or greater than food/cosmetic grade (P≥2).

The method is characterised by a sample cleaning/purification step (II) by breaking down the cyanobacterial/algal cells by ultrasonication in an aqueous solution of ammonium sulphate, and simultaneous extraction of water-soluble compounds other than phycobiliproteins (note that phycobiliproteins are extracted only marginally in this step); a step of extracting the phycobiliproteins (III) made by using water or aqueous solutions (FIG. 3).

In practice, the method uses an inverse logic to the traditional one, as it first (step II) aims to purify the sample, eliminating the contaminating molecules and then it (step III) extracts the compounds of interest (the phycobiliproteins) from the biomass. In addition, the method advantageously includes the processes of cell disruption and pigment purification in one step.

A further object of the present invention is a process for producing phycobiliproteins of analytical purity, which exploits the method of the invention as a step of pre-purifying a cyanobacterial and/or algal biomass.

Advantages of the Invention

The method makes it possible to obtain phycobiliproteins whose grade is equal to or higher than food/cosmetic grade, without resorting to post-extraction purification steps. Cell disruption (lysis) and product purification are carried out in a single step upstream of the pigment extraction process; they are subsequently recovered, obtaining a very concentrated extract of relatively high purity.

These features reduce production times and costs and make the method an excellent candidate for industrial-scale use.

The process of cell disruption by ultrasonication in the presence of ammonium sulphate enables cells to be broken down rapidly (in a few minutes), minimising the loss of phycobiliproteins and promoting the elimination of contaminants.

It should also be noted that, since the phycobiliprotein extract can be obtained already very concentrated, it can be freeze-dried according to techniques known to the person skilled in the art, without the need to concentrate it beforehand, possibly combining it with excipients and/or diluents suitable for freeze-drying (e.g. stabilisers, cryopreservatives).

Production times are reduced, to the advantage of product quality; it also avoids the development of an unpleasant odour, as is often the case in long-lasting extraction processes, carried out at room temperature.

The elimination of the purification step downstream of extraction is a key achievement, particularly beneficial for large-scale production and biotechnology applications, which meets the industry's need for a simple, reliable, time- and cost-efficient method to achieve sustainable production of commercially high valuable phycobiliproteins.

Moreover, the method of the invention enables aqueous extracts to be obtained, completely eliminating the use of organic solvents, which not only destabilise the structure of the phycobiliproteins, but also make the final product potentially toxic.

DESCRIPTION OF THE DRAWINGS

FIG. 4: Absorbance spectra of diluted solutions of *Spirulina* extracts obtained by applying the method of the invention (Extract of Sample 3: cleaning solution AS 1M, extracting solution NaCl 0.1 M; Extract of Sample 4: cleaning solution AS 1M, extracting solution $CaCl_2$ 0.1 M). The control extracts were obtained by freeze-thawing the biomass suspended in the extracting solution (Extract of Sample 1: control in NaCl 0.1 M; Extract of Sample 2: control in $CaCl_2$ 0.1 M).

FIG. 5: Absorbance spectra of diluted solutions of *Spirulina* extracts obtained by applying the method of the invention (Extract of Sample 1: control in NaCl 0.1 M freeze-thawed; Extract of Sample 2: cleaning solution AS 1 M, extracting solution NaCl 0.1 M; Extract of Sample 3: cleaning solution AS 1 M, extracting solution MilliQ water). The control extract was obtained by freeze-thawing the biomass suspended in the extracting solution (Extract of Sample 1: control in NaCl 0.1 M).

FIG. 8: Absorbance spectra of diluted solutions of *Spirulina* extracts obtained from freeze-dried biomasses, by applying the method of the invention. Control examples are shown (Extract of Sample 1: control in NaCl 0.1 M; Extract of Sample 2: control in $CaCl_2$ 0.1 M; Extract of Sample 3: cleaning solution AS 1.5 M, extracting solution NaCl 0.1 M; Extract of Sample 4: cleaning solution AS 1.5 M, extracting solution $CaCl_2$ 0.1 M; Extract of Sample 5: cleaning solution AS 1.5 M, extracting solution $CaCl_2$ 0.1 M).

FIG. 9: Absorbance spectra of *Porphyridium cruentum* extracts obtained by applying the method of the invention. (Extract of Sample 1: cleaning solution AS 1 M, extracting solution $CaCl_2$ 0.1 M; Extract of Sample 2: cleaning solution AS 1.5 M, extracting solution $CaCl_2$ 0.1 M).

FIG. 13: Yield (average) and purity (average) of the process for extracting phycobiliproteins from fresh (wet) *Spirulina* biomass as a function of the ammonium sulphate concentration of the cleaning solution. The extracting solution consists of $CaCl_2$ 0.1 M, the extraction time is 4 hours at room temperature. Two tests were performed for each concentration of AS.

FIG. 14: Absorbance spectra of diluted solutions of *Spirulina* extracts obtained by applying the method of the invention, testing different extracting solutions. The extracts were diluted to perform the spectrophotometric measurements (Samples 1 and 2: extracting solvent sugar table 0.1 M; Samples 3 and 4: extracting solvent sorbitol 0.1 M; Samples 5 and 6: extracting solvent Na-acetate 0.1 M pH 5.1; Samples 7 and 8: extracting solvent $CaCl_2$ 0.05 M (control)).

FIG. 15: Absorbance spectra of diluted solutions of *Spirulina* extracts obtained by applying the method of the invention, testing different extracting solutions. The extracts were diluted to carry out spectrophotometric measurements (Samples 1 and 2: extracting solvent sugar table 0.1 M; Samples 3 and 4: extracting solvent sorbitol 0.1 M; Samples 5 and 6: extracting solvent Na-acetate 0.1 M pH 5.5; Samples 7 and 8: extracting solvent Na-acetate 0.1 M pH 5.1; Samples 9 and 10: extracting solvent $CaCl_2$ 0.1 M (control); Samples 11 and 12: extracting solvent $CaCl_2$ 0.05 M (control)).

FIG. 18: Absorbance spectra of diluted solutions of *Spirulina* extracts obtained by applying the method of the invention, using different concentrations of table sugar (sucrose) in the extracting solution. The extracts were diluted to perform the spectrophotometric measurements (Samples 1 and 2: sugar table 0.05 M; Samples 3 and 4: sugar table 0.1 M; Samples 5 and 6: sugar table 0.5 M; Samples 7 and 8: sugar table 1 M).

FIG. 24: Absorbance spectra of *Spirulina* extracts obtained by applying the method of the invention, using extracting solutions of carbohydrates of different concentrations (Sample 1: dextran 30%; Sample 2: dextran 10%; Sample 3: dextran 1%; Sample 4: dextrin 5%). The extracts were diluted to perform the spectrophotometric measurements.

DETAILED DESCRIPTION OF THE INVENTION

As already mentioned in the summary of the invention, the object of the present patent application is a method for extracting from cyanobacterial and/or algal biomasses phycobiliproteins having a purity P degree≥2.0; in particular, the method comprises the following steps I) arranging a cyanobacterial and/or algal biomass;

II) cleaning the cyanobacterial and/or algal biomass, such cleaning step comprising the sub-steps of IIa) submitting the cyanobacterial and/or algal biomass to cell lysis by ultrasonication, said cyanobacterial and/or algal biomass being suspended in an aqueous cleaning solution of ammonium sulphate having a concentration between 0.4 and 2.0 M, to obtain a biomass lysed suspension;

IIb) separating from the suspension of the lysed biomass the cleaning solution and isolating the precipitate of the lysed biomass, such precipitate being a cleaned sample of the biomass;

III) extracting the phycobiliproteins from the biomass cleaned sample, said extraction step comprising the sub-steps of IIIa) suspending the biomass cleaned sample in an extracting solution selected from water and aqueous solutions, to obtain a suspension of the biomass cleaned sample;

IIIb) separating from the suspension of the biomass cleaned sample the extracting solution and isolating the supernatant, to obtain an extract of phycobiliproteins having purity P degree≥2.0.

It should be noted that, for the purposes of the present invention, the purity P degree is calculated as the ratio of the maximum absorbance value of the extracted phycobiliprotein, preferably phycocyanin or phycoerythrin, to the absorbance value at 280 nm ($A_{max}/A_{280}$), which is related to the total amount of protein in the product.

It should be noted that a P degree between about 2.0 and 4.5 ($2 \leq P \leq 4.5$) identifies a phycobiliprotein extract suitable for cosmetic, nutraceutical, food, reactive (as a reagent), analytical use or as fluorescent marker.

A P degree between about 2.0 and 3.7 ($2 \leq P \leq 3.7$) identifies instead a phycobiliprotein extract suitable for cosmetic, nutraceutical, food use or as a fluorescent marker.

According to a preferred embodiment, the method of the invention allows obtaining phycobiliprotein extracts having a purity P degree between 2.0 and 4.5.

Preferably, the method of the invention allows obtaining phycobiliprotein extract with a purity P degree between about 2.0 and 4.2, preferably between about 2.0 and 4.0, preferably between 2.0 and 3.7, preferably between about 2.0 and 3.5, preferably between about 2.5 and 3.5.

Advantageously, the method allows obtaining phycobiliprotein extracts in water or aqueous solutions.

Figure 1:
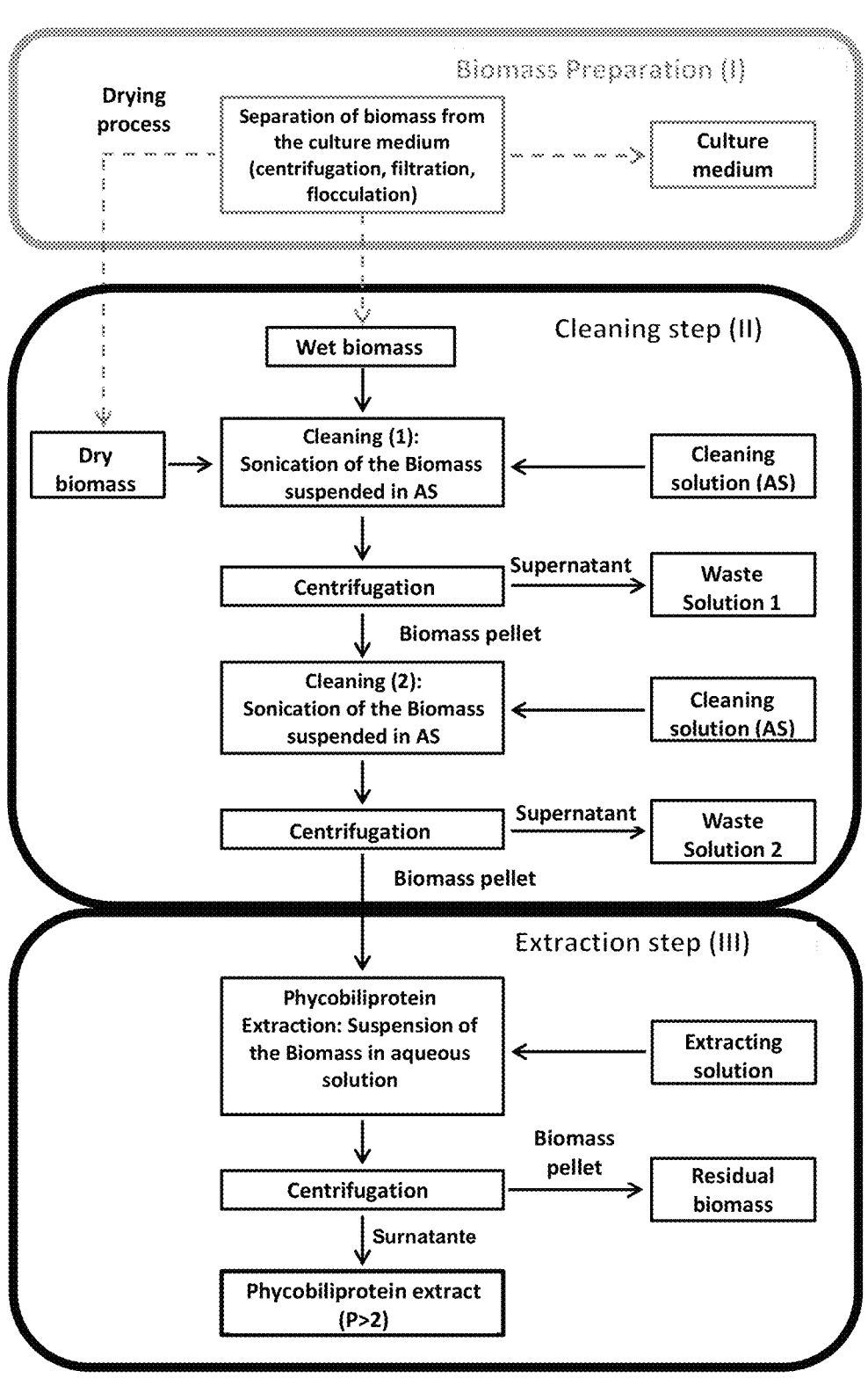
FIG. 1: Flow chart of the method of the invention.
Figure 2:
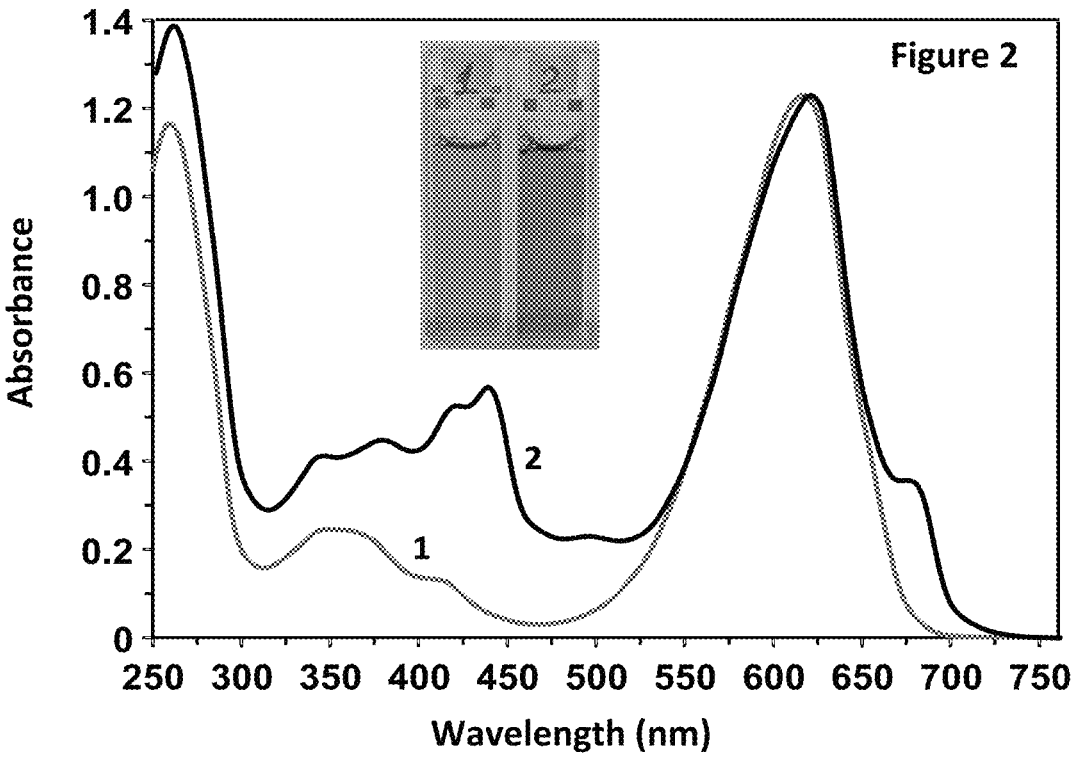
FIG. 2: Absorbance spectra of solutions (NaCl 0.1 M) of raw extracts of phycobiliproteins (PC+APC), obtained after cell lysis of *Spirulina* biomasses with two different processes: 1) freeze-thawing (curve 1)—the sample solution in cuvette 1 (inset) appears blue; 2) freeze-thawing+sonication (curve 2)—the solution in cuvette 2 (inset) appears green, as the lysed sample contains carotenoid and chlorophyll residues that alter the blue colour of the phycobiliprotein solution.

With reference to the appended FIG. 1, the main steps of a preferred embodiment of the method of the invention are schematically represented in a flow chart; for the purpose of greater intelligibility of the invention, the method will be described below step by step, indicating, where necessary, the preferred embodiments of the method.

It should be noted that, for the purposes of the present invention, the expression "about", with reference to the purity values, indicates a variation of ±0.30.

Step I: Providing Cyanobacterial and/or Algal Biomass

For the purposes of the present invention, the cyanobacterial and/or algal biomass is preferably selected from fresh biomasses or dehydrated biomasses. The best results are obtained with fresh biomasses and, in this respect, fresh biomass is preferred to dry biomass.

According to a preferred embodiment, the cyanobacterial and/or algal biomass comprises *Arthrospira platensis* (*Spirulina*), *Porphyridium cruentum*, or combinations thereof. Preferably, the cyanobacterial biomass consists of *Arthrospira platensis* or *Poprhyridium cruentum*.

Preferably, the fresh biomasses suitable for the purposes of the invention are wet biomasses, having a water content between about 74% and about 90%.

Examples of fresh biomasses suitable for carrying out the method are cell cultures of the cyanobacterial and/or algal species of selection.

Dehydrated biomass is defined as a biomass that has been submitted to dehydration or drying treatments, such as freeze-drying or spray-drying.

Preferably, the dehydrated biomass has a water content of <4%.

It should be noted that, for the purposes of the invention, it is generally important that the starting biomass contains intact and non-lysed cells, to avoid loss and degradation of phycobiliproteins in solution; in this respect, for example frozen biomasses or freeze-dried biomasses in powder form are not ideal (since freeze-drying, as such, does not generally cause significant cell lysis, but the pulverisation process following freeze-drying causes the more or less complete disruption of cyanobacterial and/or algal cells due to mechanical friction).

According to a preferred embodiment, when the cyanobacterial and/or algal biomass is in the form of cell culture (raw cyanobacterial and/or algal biomass), step I of the method comprises one or more sub-steps of preparing the sample.

Preferably, when the cyanobacterial and/or algal biomass is in the form of cell culture, step I of the method comprises a sub-step of separating the cells (Ia) from the culture medium, so as to obtain the cyanobacterial and/or algal biomass.

Preferably, cell separation is carried out by methods such as for example filtration and centrifugation.

When the cell culture is *Arthrospira platensis*, the step (Ia) of separating is preferably carried out by filtration; this filtration can be carried out with conventional means, such as nylon filters (porosity 21 μm), glass microfibre filters, vibrating screen. Any person skilled in the art having ordinary knowledge in the field can, without any effort, identify alternative techniques to those listed above for preparing the sample for the subsequent treatment steps of the method of the invention.

According to an alternative embodiment, when the cell culture is *Porphyridium cruentum*, the sub-step (Ia) of separating is preferably carried out by centrifugation; this centrifugation is preferably carried out for a time interval between 10 and 30 minutes at a centrifugal acceleration between 2,500×g and 12,000×g, preserving the precipitate (pellet), so as to obtain the biomass separated from the culture medium.

The cyanobacterial and/or algal biomass, prepared in this way, can be directly suspended in the cleaning solution of ammonium sulphate in order to proceed to step II of cleaning the sample.

It should be noted that, preferably, centrifugation or filtration of the cell culture is carried out twice on the same sample, possibly by rinsing the biomass separated from the culture medium with water (potable or distilled or deionised).

When the cyanobacterial and/or algal biomass is in freeze-dried form, the biomass is already suitable to be submitted to the cleaning step and it is preferable to suspend it directly in the cleaning solution, without previously rehydrating the sample in water; in fact, rehydration in water could in fact reduce the yield or purity of the extract due to the partial passage of the phycobiliproteins into solution.

Step II: Cleaning the Cyanobacterial and/or Algal Biomass

One of the main distinguishing features of the method of the invention is the cleaning step, which makes it possible to carry out the cell disruption process (lysis) and the sample purification process in a single step.

It should be noted that, in the state of the art, ammonium sulphate is a salt commonly used in separation/purification processes by salting-out (precipitation) of phycobiliproteins, downstream of the extraction (see CN109879943A described in the state of the art). In the method of the invention, on the other hand, ammonium sulphate is used upstream of the extraction and has the function (as a cleaning solution) of reducing/preventing the passage of the phycobiliproteins into solution, which remain trapped within the cells.

The literature generally reports salting-out conditions of phycobiliproteins in which the degree of saturation of ammonium sulphate (AS) is at least equal to 50% (>2 M, about 2.03 M). For phycoerythrin, processes in which the degree of saturation of AS is 45% (about 1.8 M) are also provided. In phycobiliprotein purification processes that apply several salting-out steps, a first fraction is usually precipitated under AS saturation conditions between 20% and 30%; this first fraction is discarded. A second fraction is then precipitated, increasing the degree of saturation; this second fraction is collected.

The aqueous cleaning solution of ammonium sulphate is used, in the method of the invention, in molar concentration between 0.4 and 2.0 M (AS 1 M is equivalent, at 20° C., to a degree of saturation of about 24.6%, 1.5 M to about 37%, 2 M to about 49%); in this respect, it should be noted that, advantageously, the method of the invention allows to block the extraction of proteins and, consequently, their passage into solution, even under partial salting-out conditions, using concentrations of ammonium sulphate (as well as also the times of the process) that are generally lower than those commonly required to cause the precipitation of the phyco-biliproteins for the same purpose: the purification of the phycobiliproteins.

The Applicant therefore believes that the method of the invention also has an advantage in terms of reducing the consumption of ammonium sulphate for the purposes of biomass purification.

It should be noted that, as mentioned above, step II of cleaning takes place by subjecting the cyanobacterial and/or algal biomass to cell lysis by ultrasonication, while the biomass itself is suspended in the aqueous solution of AS. In other words, the Applicant believes that the operation responsible for cell lysis is ultrasonication and not the suspension of the sample in AS. Ammonium sulphate has the function of preventing the passage of the phycobiliproteins into solution.

Preferably, the aqueous cleaning solution of ammonium sulphate used for the purposes of the invention has a molar concentration between 0.4 and 1.8 M, preferably between 0.5 and 1.8 M, preferably between 0.8 and 1.6 M, preferably between 0.9 and 1.6 M.

Preferably, when the method of the invention is applied to the extraction of the phycocyanin, the aqueous solution of ammonium sulphate has a concentration between 0.9 and 1.5 M, preferably between 1.0 and 1.4 M.

Preferably, when the method is applied to the extraction of the phycoerythrin, the aqueous solution of ammonium sulphate has a concentration between 0.9 and 1.6 M, preferably between 1.2 and 1.6 M.

As stated above, it is important that the starting biomass contains intact and non-lysed cells to avoid loss and degradation of phycobiliproteins in solution. It should be noted that the use of biomasses containing intact, non-lysed cells is advantageous for the purposes of the invention when, in particular, the concentration of cleaning solution is less than or equal to 1.1 M, preferably between 0.4 M and 1.1 M (although the use of biomasses containing intact, non-lysed cells is applicable to the whole interval of concentrations 0.4-2.0 M of cleaning solution). A starting biomass containing already lysed cells can be used for concentrations of cleaning solution greater than or equal to 1.2 M, preferably between 1.3 M and 2.0 M. By way of non-limiting representation, see Embodiment example No. 5.

According to the preferred embodiment, the cleaning solution and the cyanobacterial and/or algal biomass are combined in a volume (ml)/dry weight ratio of the biomass (g) between 10:1 and 1000:1, preferably between 10:1 and 700:1, preferably, between 15:1 and 300:1, preferably, between 20:1 and 100:1.

It should be noted that dry weight of the biomass is defined as:

the weight of the freeze-dried biomass, or in the case of cell cultures of cyanobacterial and/or algal biomass or biomass suspensions in aqueous solutions, the weight of the dried biomass, by applying the following process:

Filter a known volume of culture or biomass suspension on a GF/C glass microfibre filter (previously placed in an oven at 105° C. for one hour, allowed to cool and weighed);

Wash with 30-50 mL of distilled or deionised water;

Dry in an oven at 105° C. for at least 3 hours, or at 70° C. for at least 24 hours;

Allow to cool, then weigh (subtract tare).

Preferably, sub-step IIa of ultrasonication is carried out at a frequency between 19 and 26 kHz, preferably between 22 and 26 kHz, preferably between 23 and 26 kHz.

Preferably, sub-step IIa of ultrasonication is carried out for a time interval between 1 and 20 minutes, preferably between 2 and 8 minutes.

Preferably, sub-step IIa of ultrasonication is carried out by performing a plurality of sonication cycles, each lasting between 2 and 8 minutes, preferably by performing 2 to 4 sonication cycles, each lasting between 2 and 8 minutes, preferably by performing 2 sonication cycles, each lasting between 2 and 8 minutes.

According to a preferred embodiment, ultrasonication is carried out in cold water or an ice/water bath, to prevent the increase in temperature of the suspension from causing thermal denaturation of the phycobiliproteins, which are not very resistant to temperatures above 40-50° C.

Figure 3:
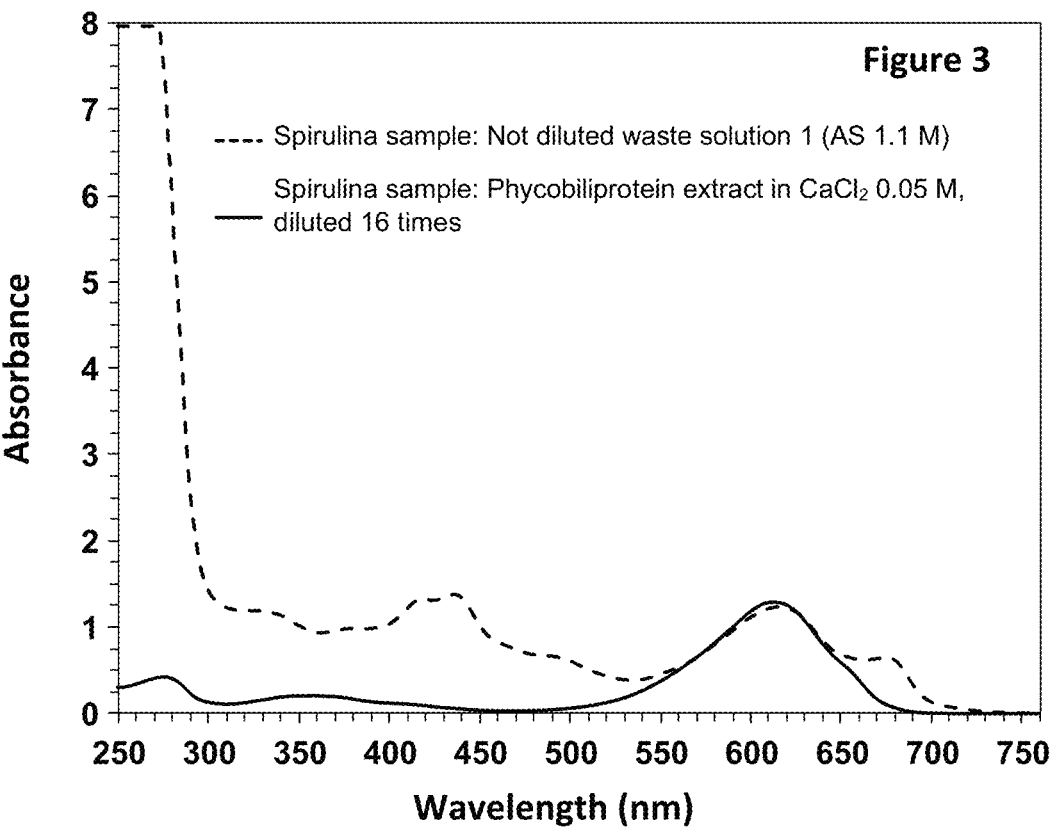
FIG. 3: Absorbance spectra of the washing solution (waste solution 1) of a sample of *Spirulina* after sonication in AS 1.1 M (not diluted), and of the phycobiliprotein extract of the same sample of *Spirulina* in $CaCl_2$ 0.05 M. The phycobiliprotein extract was diluted 16 times to perform the spectrophotometric measurement.

The use of sonication on the sample suspended in the cleaning solution advantageously allows isolating the phycobiliproteins from the solution, preventing or in any case greatly slowing down the extraction process, while favouring the extraction of chlorophyll and/or carotenoids (see FIG. 3), which can influence the final colour of the extract.

It should be noted that the sub-step IIb of separating can be carried out by means of separation technologies known to the person skilled in the art, such as for example centrifugation and filtration; in the case of filtration, a particularly preferred form of separation is tangential flow filtration.

According to a preferred embodiment, the sub-step IIb of separating comprises or consists of a centrifugation sub-step, wherein the lysed biomass suspension is centrifuged and the lysed biomass precipitate is isolated from the cleaning solution, such precipitate being the biomass cleaned sample.

It should be noted that a biomass cleaned sample is defined as a sample comprising phycobiliproteins trapped in the lysed cells of the cyanobacterial and/or algal biomass; alternatively or in addition to the foregoing definition, for the purposes of the invention a biomass cleaned sample is defined as a sample not comprising free or dissolved phycobiliproteins.

Preferably, the centrifugation sub-step is carried out at a centrifugal acceleration at least equal to 3,000×g, preferably between 3,000×g and 15,000×g.

Preferably, the centrifugation sub-step is carried out for a time interval between 10 and 60 minutes, preferably between 10 and 30 minutes, preferably between 10 and 15 minutes.

According to a preferred embodiment, sub-step IIb of separating comprises a sub-step of leaving (with or without stirring) the suspension, after separation, at a temperature between 4° C. and 35° C., preferably between 15° C. and 30° C.

Preferably this step of leaving is carried out for a time interval between 10 and 30 minutes.

According to a preferred embodiment, step II of cleaning the biomass is carried out at least once; preferably step II of cleaning the biomass is carried out twice.

Step III: Extracting the Phycobiliproteins from the Biomass Cleaned Sample

The extraction of the phycobiliproteins is carried out by suspending the biomass cleaned sample in an extracting solution, to obtain a suspension of the biomass cleaned sample.

The extracting solution is selected between water and aqueous solutions, wherein such aqueous solutions are preferably selected from: inorganic salt aqueous solutions, buffer aqueous solutions, carbohydrates aqueous solutions, polyol aqueous solutions, etc.

It should be noted that carbohydrates preferably means monosaccharides, disaccharides and polysaccharides.

More in detail, the extracting solution is preferably selected from the group consisting of:

water, preferably potable, deionised, distilled water or ultrapure water (resistivity>18.18 MW—note that ultrapure water, although usable in practical terms, is not very widespread in the industrial sector due to its high cost);

inorganic salt solutions, preferably inorganic salt solutions having a concentration between 0.01 M and 0.5 M; preferably between 0.05 and 0.2 M; preferably between 0.05 M and 0.1 M;

buffer solutions, preferably buffer solutions having a pH between 4.5 and 7.2; preferably between 5.0 and 7.0; preferably between 5.5 and 6.5;

solutions of monosaccharides, preferably solutions of monosaccharides having a concentration between 0.01 and 1.2 M; preferably between 0.05 and 1 M; preferably between 0.05 and 0.5 M;

solutions of disaccharides, preferably solutions of disaccharides having a concentration between 0.01 M and 1.2 M; preferably between 0.05 and 1 M; preferably between 0.05 M and 0.5 M;

solutions of polysaccharides, preferably solutions of polysaccharides having a concentration between 0.01% and 15%, preferably between 0.01% and 10%;

polyol solutions, preferably polyol solutions having a concentration between 0.01 and 1.6 M, preferably between 0.01 and 1M, preferably between 0.05 and 0.5 M.

Preferably, the inorganic salts suitable for the preparation of extracting aqueous solutions are selected from sodium chloride and calcium chloride.

It should be noted that, according to a preferred embodiment, when the cyanobacterial and/or algal biomass comprises or consists of *Porphyridium cruentum*, the extracting aqueous solution of inorganic salts is a calcium chloride solution.

Preferably, buffers suitable for the preparation of extracting aqueous solutions are selected from the group consisting of (sodium) citrate, (sodium) acetate, (sodium or potassium) phosphate.

Preferably, the monosaccharides suitable for the purposes of the invention are selected from the group consisting of: glucose, fructose, galactose.

Preferably, the disaccharides suitable for the purposes of the invention are selected from the group consisting of: sucrose, maltose, lactose and trehalose.

Preferably, the polysaccharides suitable for the purposes of the invention are selected from the group consisting of xanthan gum, dextran and dextrin.

It should be noted that, according to a preferred embodiment, when the cyanobacterial and/or algal biomass comprises or consists of *Porphyridium cruentum*, the extracting aqueous solution of carbohydrates is a solution of monosaccharides or disaccharides.

Preferably, the polyols suitable for the purposes of the invention are selected from sorbitol, mannitol and xylitol.

Preferably, the extracting solution and the biomass are combined in a volume (ml)/dry weight ratio of the biomass (g) between 20 and 365, preferably between 26 and 250, preferably between 26 and 200, preferably between 30 and 150.

It should be noted that sub-step Mb of separating can be carried out by means of separation technologies known to the person skilled in the art, such as for example centrifugation and filtration; in the case of filtration, a particularly preferred form of separation is tangential flow filtration.

According to a preferred embodiment, sub-step Mb of separating comprises or consists of a centrifugation sub-step, wherein the suspension of the biomass cleaned sample is centrifuged and the supernatant is isolated from the extracting solution, to obtain the phycobiliprotein extract having a purity P degree$\geq$2.0.

According to a preferred embodiment, the centrifugation sub-step is carried out at a centrifugal acceleration at least equal to 3,000×g, preferably between 3,000×g and 20,000×g.

According to a preferred embodiment, the centrifugation sub-step comprises a sub-step of leaving the suspension (with or without stirring), after centrifugation, at a temperature between 4° C. and 35° C., preferably for a time interval between 30 minutes and 25 hours.

According to a preferred embodiment, when the biomass comprises or consists of *Arthrospira platensis* (*Spirulina*), sub-step Mb of separating comprises a sub-step of leaving the suspension (with or without stirring), after separation, at a temperature between 15° C. and 35° C., preferably between 15° C. and 30° C. and for a time interval between 30 minutes and 6 hours, preferably between 4 and 5 hours.

According to a preferred embodiment, when the biomass comprises or consists of *Porphyridium cruentum*, the step Mb of separating comprises a sub-step of leaving the suspension (with or without stirring), after separation, at a temperature between 4° C. and 8° C. and for a time interval between 30 minutes and 25 hours, preferably between 15 and 25 hours.

According to a preferred embodiment, sub-step Mb is repeated a second time on the supernatant (extract) obtained by separation from the suspension of the biomass cleaned sample. Sometimes, after the first separation, the phycobilibrotein extract still has suspended bodies, typically a veil at the surface and cellular debris that detaches from the precipitate when the supernatant is withdrawn; a second separation cycle therefore has the purpose of eliminating these suspended bodies.

In order to eliminate the suspended bodies present in the supernatant, the second separation cycle can be carried out by centrifugation or filtration.

It should be noted that the extract obtained from the extraction step III is the definitive extract obtainable by the method of the invention. In other words, the method of the invention, as a method for producing a crude extract of phycobiliproteins, preferably characterised by a purity P degree$\geq$2.0, does not comprise any step of purifying the sample downstream of extraction step III.

The phycobiliprotein extract obtained from the extraction step III is in fact highly concentrated and, as such, if appropriate excipients and/or diluents are possibly added, it can already be freeze-dried without having to previously concentrate it, using techniques known to the person skilled in the art. This is particularly true for extracts obtained by combining the extracting solution and the biomass in a volume (ml)/dry weight (g) ratio of less than 40-70.

It should be noted that the extract obtained from the extraction step III is a raw extract (or crude extract) of phycobiliproteins. The raw extract (or crude extract) of phycobiliproteins is defined as the extract obtained by isolation and separation of the phycobiliproteins from the biological sample in which they were originally contained (i.e., obtained by applying the extraction process directly to the source of phycobiliproteins). In other words, a raw extract of phycobiliproteins contains the proteins as isolated and separated from the biomass of origin, regardless of their purity degree. Any extracts that may be obtained by subsequent handling of the raw extract (or crude extract) are to be considered purified extracts (and no longer raw or crude extracts).

According to a preferred embodiment, the method comprises the further step W of freeze-drying the phycobiliprotein extract after mixing the extract with excipients and/or diluents suitable for cosmetic, nutraceutical, food use or as a fluorescent marker.

Depending on market requirements, the extract can be submitted to sterilization, after freeze-drying, by filtration with filters having 0.45 μm or 0.22 μm porosity. It should be noted that filtration also has the function of eliminating any suspended bodies, consisting of biomass residues, which are sometimes present after centrifugation.

Phycobiliprotein Extract

It should be noted that the method of the invention allows obtaining phycobiliprotein extracts of food, cosmetic, reactive (as a reagent) and analytical grade that are characterized by a purity P degree≥2, preferably between about 2.0 and 4.5, preferably between about 2.0 and 4.2, preferably between about 2.0 and 4.0, preferably between about 2.0 and 3.7, preferably between about 2.5 and 3.5, without resorting to costly purification steps downstream of the extraction.

These phycobiliprotein extracts find application in cosmetics, e.g. for the formulation of skin moisturising products, for cosmetic colouring (eyeshadow, lipstick, mask, etc.), but also for colouring the coatings of pharmaceutical products (coating for tablets, capsules);

in nutraceuticals, e.g. as a protein supplement, with a high content of essential amino acids, with high antioxidant and immunostimulating power;

in the food industry, e.g. for colouring food products that can avoid high temperatures, such as dairy products, ice creams, powdered drinks, cake fillings, milkshakes, candy products, etc;

as fluorescence agents (in particular allophycocyanin and phycoerythrin), e.g. fluorescent antibody markers, in immunological analysis, especially since they have no toxic effects. For example, immunoglobin-conjugated phycobiliproteins, protein A and avidin have been developed in fluorescent probes and have been widely used in histochemistry, fluorescence microscopy, flow cytometry, fluorescence-activated cell sorting and fluorescence immunoassays;

in the analytical field, e.g. as a visual marker for liquid chromatography and gel electrophoresis; for in vitro studies concerning the light absorbing properties that are characteristic of phycobiliproteins.

Preferably, the phycobiliprotein extract obtained with the method of the present invention is an extract comprising phycocyanin and allophycocyanin, when obtained from cyanobacterial biomasses, preferably from *Arthrospira platensis* (*Spirulina*).

It should be noted that phycocyanin and allophycocyanin extracts have a purity P in phycocyanin preferably between about 2.0 and 4.0.

Preferably, the phycobiliprotein extracts from *Arthrospira platensis* comprise phycocyanin and allophycocyanin with each other in a weight ratio between 2.30 and 6.00; preferably between 2.50 and 4.00; preferably between 2.70 and 3.50.

Preferably, the extract obtained with the method of the present invention is a phycoerythrin extract (PC and APC content less than 20% of the total phycobiliprotein content), when obtained from algal biomasses, preferably from the red alga *Porphyridium cruentum* (B-phycoerythrin).

It should be noted that B-phycoerythrin extracts from *Porphyridium cruentum* have a P purity in B-phycoerythrin preferably between 2.5 and 4.2.

Process for Purifying Phycobiliproteins

A further object of the present invention is a process for purifying phycobiliproteins from cyanobacterial and/or algal biomasses, the resulting phycobiliproteins having an analytic purity (P) degree higher than 4, comprising the method of the invention as a step of pre-purifying a cyanobacterial and/or algal biomass to obtain a raw extract of further purifiable phycobiliproteins.

For example, the method according to the present invention may be used for the production of raw extracts of phycobiliproteins suitable to be submitted subsequently as described in International Application No. PCT/IB2019/054619, the text of which is incorporated herein by reference.

More specifically, the process for purifying phycobiliproteins from cyanobacterial and/or algal biomasses, characterised by an analytic purity (P) degree higher than 4, comprises the following steps:

Pi) extracting from cyanobacterial and/or algal biomasses phycobiliproteins, by performing the method of the present invention, so as to obtain a raw extract of phycobiliproteins having a purity P degree≥2.0;

Pii) performing at least one purification cycle of the raw extract through the passage of a saline aqueous solution of said raw extract over a hydrophilic porous membrane having a low protein binding capacity, wherein said aqueous saline solution of said raw extract of phycobiliproteins is an aqueous solution of a salt S with a concentration $[S]_1$ capable of inducing selective and reversible binding of the phycobiliproteins to said membrane;

Piii) desorbing the retentate bound to said membrane by washing with a solvent selected from the group consisting of water, an aqueous solution of said salt S at a concentration $[S]_2 < [S]_1$, and an aqueous solution of a salt S' which is a stronger chaotropic agent than said salt S.

The salt S is preferably selected from ammonium sulphate and sodium sulphate. The aqueous solution of salt S' is selected preferably from a sodium chloride aqueous solution and phosphate buffered saline.

The hydrophilic porous membrane that can be used in this process may be for example a flat, hollow-fibre, capillary or tubular membrane made of hydrophilic material, selected for example from polycarbonate or PVDF (polyvinylidene fluoride); preferably the membrane material is PVDF. There are several commercial microfiltration membranes of this type, which can be used successfully in the present process.

17

EXAMPLES

For illustrative and non-limiting purposes, embodiment examples of the method subject-matter of the present invention are reported below.

EX. 1: Extraction of Phycobiliproteins (Phycocyanin and Allophycocyanin) from a Fresh (Wet) Biomass of *A. platensis* (*Spirulina*): Relative Yield of the Extract Obtained with the Method of the Invention Compared to a Control Extract An aliquot of *A. platensis* cell culture was filtered using a nylon filter (mesh size=21 μm), to separate the biomass from the culture medium. The biomass was washed with deionised water on the same filter and resuspended with MilliQ ultrapure water.

The biomass suspension was divided into 4 aliquots (Sample 1-4), the samples centrifuged (15 min, 12000×g, 15° C.), the supernatant was removed and the biomass pellet recovered for the extraction of the phycobiliproteins.

Samples 1 and 2 were used as controls: they were suspended in 7 mL of extracting solution (Sample 1 in NaCl 0.1 M, Sample 2 in $CaCl_2$ 0.1 M) and submitted to 3 freeze-thawing cycles between −20° C. and room temperature (20-25° C.). The freezing cycles lasted 2 hours, except for the last cycle which lasted all night. After the freeze-thawing treatment, the suspension was kept at 4° C. for 24 hours and subsequently centrifuged for 30 minutes (12000×g, T=15° C.). The supernatant (raw extract) was collected and the phycobiliprotein content (equation 1 and 2), and PC purity (P, equation 3) were determined by spectrophotometric analysis.

$$[PC]=(A_{615}-0.474A_{652})/5.34 \qquad \text{Equation (1):}$$

$$[APC]=(A_{652}-0.208A_{615})/5.09 \qquad \text{Equation (2):}$$

$$P=A_{615}/A_{280} \qquad \text{Equation (3):}$$

$A_{615}$ is the absorbance at 615 nm (absorbance maximum of PC) and $A_{652}$ is the absorbance at 652 nm (absorbance maximum of APC); $A_{280}$ is the absorbance at 280 nm (absorbance relative to the total protein content of the sample).

Samples 3 and 4 were submitted to the method of the invention: the samples were suspended in 9 mL of cleaning solution (1 M ammonium sulphate—AS) and sonicated for 2 minutes (power 100%, pulsation 0.6 s, sonotrode S2, Hielscher Ultrasonic Processor UP200S, 200 W, 24 kHz) in an ice/water bath. The suspensions were stirred at room temperature at 250 rpm for 20 minutes by means of an orbital shaker, centrifuged (15 min, 12000×g, 15° C.) and the supernatant removed.

The step of cleaning/cell lysis was repeated a second time.

After that, the biomass pellets were suspended in 5 mL of extracting solution (Sample 3 in NaCl 0.1 M, Sample 4 in $CaCl_2$ 0.1 M), the suspensions stirred at room temperature at 250 rpm for 4 hours by means of an orbital shaker, centrifuged (30 min, 12000×g, 15° C.), the supernatant (extract) was recovered and the phycobiliprotein content (equation 1 and 2), as well as PC purity (P, equation 3) were determined by spectroscopic analysis (FIG. 4 and Table 1).

18

TABLE 1

| | % yield (Y) (compared to the amount of PC and APC in the control extract) and purity (P) of PC of the Spirulina extract obtained using the method of the invention. | | | | |
|---|---|---|---|---|---|
| Sample | Extracting solution | $Y_{PC}$ % | $Y_{APC}$ % | $Y_{PC+APC}$ % | $P_{PC}$ |
| 3 | NaCl | 99.50 | 89.67 | 96.90 | 2.77 |
| 1 control | NaCl | 100 | 100 | 100 | 1.61 |
| 4 | $CaCl_2$ | 101.15 | 142.57 | 109.39 | 3.20 |
| 2 control | $CaCl_2$ | 100 | 100 | 100 | 2.37 |

EX. 2: Extraction of Phycobiliproteins (Phycocyanin and Allophycocyanin) from a Fresh (Wet) Biomass of *A. platensis* (*Spirulina*): Comparison Between the Extraction Yield of the Method of the Invention and the Extraction Yield of a Conventional Method An aliquot of a cell culture of *A. platensis* was filtered using a Whatman glass fibre filter (GF/C grade) to separate the biomass from the culture medium. The biomass was washed with deionised water on the same filter and the dry weight of the biomass was determined after drying at 105° C. for 4 hours.

A second aliquot of fresh culture was filtered using a nylon filter (mesh size=21 μm), to separate the biomass from the culture medium. The biomass was washed with deionised water on the same filter and resuspended with MilliQ ultrapure water.

The biomass suspension was divided into 3 aliquots (Sample 1-3), the samples centrifuged (15 min, 12000×g, 15° C.) and the supernatant removed.

Sample 1 was used as a control: it was suspended in 5 mL of extracting solution (NaCl 0.1M) and submitted to three freeze-thawing cycles between −20° C. and room temperature (20-25° C.). The freezing cycles lasted 2 hours, except for the last cycle which lasted all night. After the freeze-thawing treatment, the suspension was kept at 4° C. for 24 hours and then centrifuged for 30 min (12000×g, T=15° C.). The supernatant (raw extract) was recovered, and the phycobiliprotein content and PC purity were determined by spectrophotometric analysis (see Ex. 1).

Samples 2 and 3 were submitted to the extraction method of the invention: they were suspended in 20 mL of cleaning solution (1 M AS) and sonicated for 2 min (power 100%, pulsation 0.6 s, sonotrode S2, Hielscher Ultrasonic Processor UP200S, 200 W, 24 kHz) in an ice/water bath. The suspensions were stirred at room temperature at 250 rpm for 20 min by means of an orbital shaker, centrifuged (15 min, 12000×g, 15° C.) and the supernatant removed.

The step of cleaning/cell lysis was repeated a second time.

Afterwards, the samples were suspended in 5 mL of extracting solution (Sample 2 in NaCl 0.1 M, Sample 3 in MilliQ water) stirred at room temperature at 250 rpm for 4 hours by means of an orbital shaker, centrifuged (30 min, 12000×g, 15° C.), the supernatant (extract) recovered and the phycobiliprotein content, as well as the PC purity, determined (FIG. 5 and Table 2) by spectrophotometric analysis (see Ex. 1).

TABLE 2

% yield (Y) (mg/mg dry weight of the biomass) and purity
of spirulina extracts obtained by applying the process
of the invention. The % yield and the purity of the extract
obtained by freeze-thawing is reported as a control.

| Sample | Extracting solution | $Y_{PC}$ % | $Y_{APC}$ % | $Y_{PC+APC}$ % | $P_{PC}$ |
|---|---|---|---|---|---|
| 1 control | NaCl | 18.46 | 6.53 | 24.99 | 2.07 |
| 2 | NaCl | 17.36 | 5.10 | 22.46 | 2.85 |
| 3 | Water | 16.68 | 5.01 | 21.69 | 2.89 |

EX. 3: Extraction of Phycobiliproteins
(Phycocyanin and Allophycocyanin) from a Fresh
(Wet) Biomass of *A. platensis* (*Spirulina*):
Comparison Between Different Extracting Solutions An aliquot of a cell culture of *A. platensis* was filtered using a Whatman glass fibre filter (GF/C grade) to separate the biomass from the culture medium. The biomass was washed with deionised water on the same filter and the dry weight of the biomass was determined after drying at 105° C. for 4 hours.

Method of invention: A second aliquot of fresh culture was filtered using a nylon filter (mesh size=21 μm), to separate the biomass from the culture medium. The biomass was suspended in the cleaning solution (1 M AS).

The biomass suspension was divided into 5 aliquots (Samples 1-5) and the volume of each sample increased to 9 mL by the addition of an appropriate volume of cleaning solution. Samples were sonicated for 2 min (power 100%, pulsation 0.6 s, sonotrode S2, Hielscher Ultrasonic Processor UP200S, 200 W, 24 kHz) in an ice/water bath, stirred at room temperature at 250 rpm for 20 min by means of an orbital shaker, then centrifuged (15 min, 12000×g, 15° C.) and the supernatant removed.

The process of cleaning/cell lysis was repeated a second time.

Figure 6:
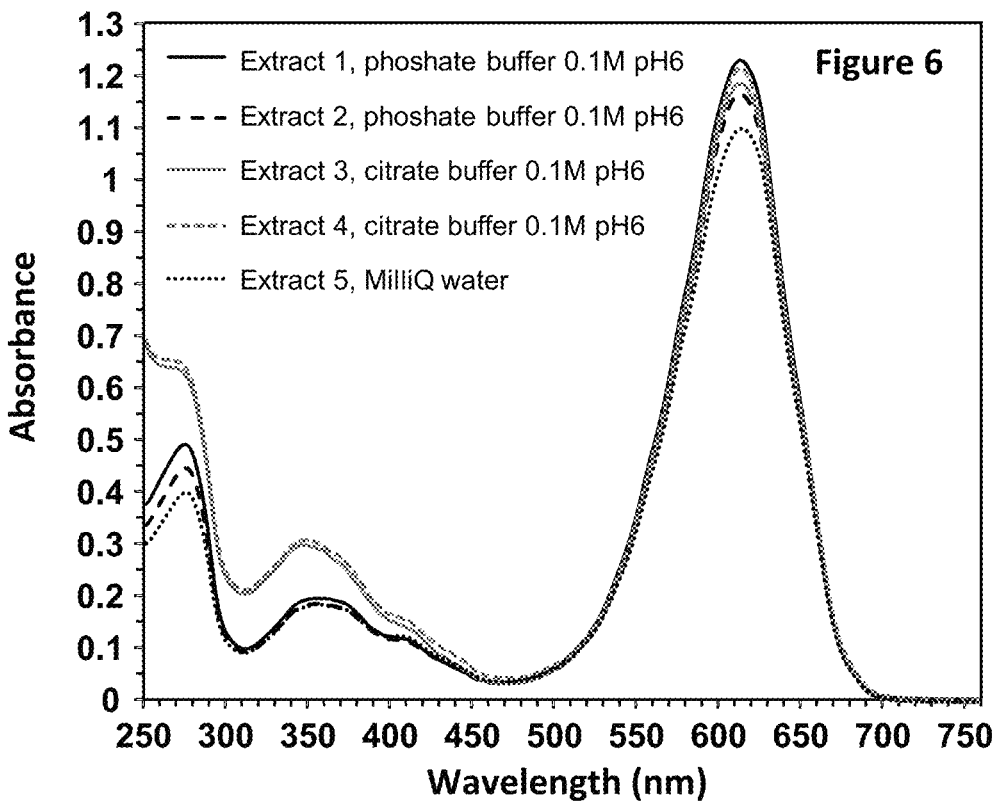
FIG. 6: Absorbance spectra of diluted solutions of *Spirulina* extracts obtained by applying the method of the invention, comparing different extracting solutions (Extract 1: phosphate buffer 0.1 M pH 6; Extract 2: phosphate buffer 0.1 M pH 6; Extract 3: citrate buffer 0.1 M pH 6; Extract 4: citrate buffer 0.1 M pH 6; Extract 5: MilliQ water).

After that, the biomass pellets were suspended in 5 mL of extracting solution (Pellets 1-2 in Na-phosphate buffer 0.1 M pH 6, Pellets 3-4 in Na-citrate buffer 0.1 M pH 6, Pellets 5 in MilliQ water), stirred at room temperature at 250 rpm for 4 hours by means of an orbital shaker, centrifuged (30 min, 12000×g, 15° C.), the supernatant (extract) recovered, the phycobiliprotein content and PC purity (FIG. 6 and Table 3) determined by spectrophotometric analysis (see Ex. 1).

TABLE 3

% yield (Y) (mg/mg dry weight of the biomass) and purity of Spirulina
extracts obtained by means of the method of the invention.

| Sample | Extracting solution | $Y_{PC}$ % | $Y_{APC}$ % | $Y_{PC+APC}$ % | $P_{PC}$ |
|---|---|---|---|---|---|
| 1 | Na-phosphate 0.1M, pH 6 | 17.10 | 5.51 | 22.61 | 2.68 |
| 2 | Na-phosphate 0.1M, pH 6 | 16.27 | 5.34 | 21.61 | 2.77 |
| 3 | Na-citrate 0.1M, pH 6 | 16.60 | 5.40 | 21.99 | 2.05 |
| 4 | Na-citrate 0.1M, pH 6 | 17.00 | 5.50 | 22.50 | 2.06 |
| 5 | Water | 15.14 | 5.17 | 20.31 | 2.91 |

EX. 4: Extraction of Phycobiliproteins
(Phycocyanin and Allophycocyanin) from a
Freeze-Dried Biomass of *A. platensis* (*Spirulina*)
(Laboratory-Grown Biomass)

Figure 7:
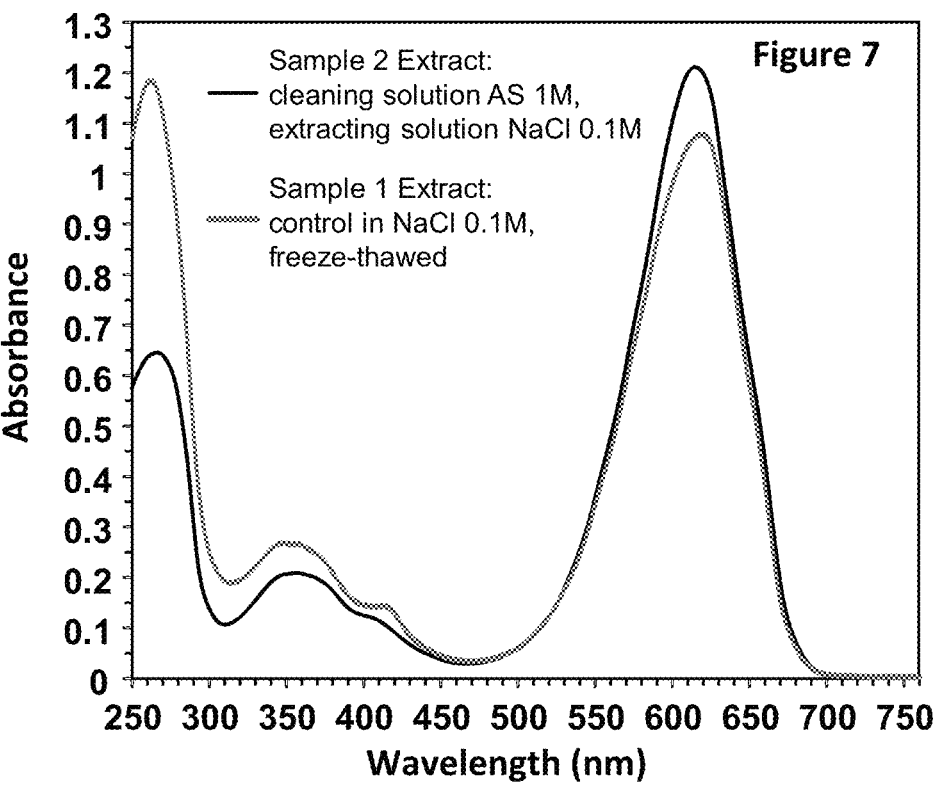
FIG. 7: Absorbance spectra of diluted solutions of *Spirulina* extracts obtained from freeze-dried biomasses, by applying the method of the invention (Extract of Sample 2: cleaning solution AS 1 M, extracting solution NaCl 0.1 M). The control extract was obtained by freezing-thawing the biomass suspended in the extracting solution (Extract of Sample 1: control in NaCl 0.1 M frozen/thawed).

Control: A raw extract of phycobiliproteins was obtained by suspending the freeze-dried powder of *Spirulina* biomass (about 50 mg, Sample 1) in 5 mL of extracting solution (NaCl 0.1 M). The suspension was submitted to three freeze-thawing cycles between −20° C. and room temperature (20-25° C.). The freezing cycles lasted 2 hours, except for the last cycle which lasted all night. After freeze-thaw treatment, the suspension was kept at 4° C. for 24 hours and centrifuged for 30 min (12000×g, T=15° C.). The supernatant (raw extract) was collected, the phycobiliprotein content and PC purity (FIG. 7 and Table 4) determined by spectrophotometric analysis (see Ex. 1).

Another sample of freeze-dried biomass was submitted to the method of the invention: the sample (Sample 2) was suspended in 5 mL of cleaning solution (1 M AS) and sonicated for 1 min (power 75%, pulsation 0.6 s, sonotrode S2, Hielscher Ultrasonic Processor UP200S, 200 W, 24 kHz) in a water/ice bath. Subsequently, the suspension was left at room temperature (without stirring) for 20 minutes, centrifuged (15 min, 12000×g, 15° C.) and the supernatant removed.

The process of cleaning/cell lysis was repeated a second time.

Afterwards, the biomass pellet was suspended in 5 mL of extracting solution (NaCl 0.1 M), left at room temperature (without stirring) for 4 hours, centrifuged (30 min, 12000×g, 15° C.), the supernatant (extract) recovered; the phycobiliprotein content and PC purity (FIG. 7 and Table 4) were determined by spectrophotometric analysis (see Ex. 1).

TABLE 4

% yield (Y) (mg/mg dry weight of the biomass) and purity of Spirulina
extract obtained by applying the method of the invention. The sample
submitted to freeze-thawing cycles was used as a control.

| Sample | Extracting solution | $Y_{PC}$ % | $Y_{APC}$ % | $Y_{PC+APC}$ % | $P_{PC}$ |
|---|---|---|---|---|---|
| 1 control | NaCl | 11.33 | 4.57 | 15.91 | 1.22 |
| 2 | NaCl | 10.26 | 3.95 | 14.21 | 2.19 |

EX. 5: Extraction of Phycobiliproteins
(Phycocyanin and Allophycocyanin) from a
Commercially Available Freeze-Dried Biomass of
*A. platensis* (*Spirulina*): Combination Ratio of
Cleaning Solution/Biomass, Extracting
Solution/Biomass Control: raw extracts of phycobiliproteins were obtained by suspending the freeze-dried powder of *Spirulina* biomass (about 50 mg) in 5 mL of extracting solution (NaCl 0.1 M Sample 1, CaCl$_2$ 0.1 M Sample 2). The cells in this biomass are already broken down and, therefore, no process was required to promote the release of the phycobiliproteins into solution. The suspensions were stirred at room temperature at 250 rpm for 4 hours by means of an orbital shaker, centrifuged (30 min, 12000×g, 15° C.), the supernatant (raw extract) recovered; the phycobiliprotein content and PC purity (FIG. 8 and Table 5) were determined by spectrophotometric analysis (see Ex. 1).

Samples of the freeze-dried biomass were submitted to the method of the invention: two samples of 50 mg and one sample of 1 g were suspended in 5 mL (Samples 3 and 4) and 25 mL (Sample 5) of cleaning solution (1.5 M AS), respectively, and sonicated for 1 minute (Sample 3 and 4) or 2 minutes (Sample 5) (power 75%, pulsation 0.6 s, sonotrode S2, Hielscher Ultrasonic Processor UP200S, 200 W, 24 kHz) in a water/ice bath. Subsequently, the suspensions were stirred at room temperature at 250 rpm for 20 minutes with an orbital shaker, centrifuged (15 min, 12000×g, 15° C.) and the supernatant removed.

The process of cleaning/cell lysis was repeated a second time.

After that, the biomass pellets were suspended in 5 mL of extracting solution (NaCl 0.1 M Sample 3, CaCl$_2$ 0.1 M Sample 4) or in 25 mL of extracting solution (CaCl$_2$ 0.1 M Sample 5), stirred at 250 rpm, at room temperature for 4 hours with an orbital shaker, centrifuged (30 min, 12000×g, 15° C.), the supernatant (extract) recovered; the phycobiliprotein content and PC purity (FIG. 8 and Table 5) were determined by spectrophotometric analysis (see Ex. 1).

TABLE 5

% yield (Y) (mg/mg dry weight (d.w.) of the biomass) and purity of Spirulina extract obtained by applying the method of the invention. The volume ratio of the cleaning or extracting solution to the dry weight of the biomass (R) is also reported.

| Sample | Extracting solution | R (v/d.w.) | $Y_{PC}$ % | $Y_{APC}$ % | $Y_{PC+APC}$ % | $P_{PC}$ |
|---|---|---|---|---|---|---|
| 1 control | NaCl | 100 | 11.48 | 3.87 | 15.35 | 0.91 |
| 2 control | CaCl$_2$ | 100 | 12.89 | 3.54 | 16.42 | 1.16 |
| 3 | NaCl | 100 | 8.88 | 2.03 | 10.91 | 2.03 |
| 4 | CaCl$_2$ | 100 | 9.36 | 1.58 | 10.95 | 2.58 |
| 5 | CaCl$_2$ | 25 | 10.27 | 1.87 | 12.15 | 1.96 |

EX. 6: Extraction of B-Phycoerythrin (B-PE) from a Dried Biomass of *Porphyridium cruentum*

Two samples of freeze-dried biomass of *Porphyridium cruentum* were submitted to the method of the invention: two samples of 50 mg were suspended in 5 mL of cleaning solution (Sample 1 in AS 1 M, Sample 2 in AS 1.5 M) and sonicated for 2 minutes (power 100%, pulsation 0.6 s, sonotrode S2, Hielscher Ultrasonic Processor UP200S, 200 W, 24 kHz) in an ice/water bath. Subsequently, the suspensions were stirred at room temperature at 250 rpm for 20 minutes with an orbital shaker, centrifuged (15 min, 12000×g, 15° C.) and the supernatant removed.

The process of cleaning/cell lysis was repeated a second time.

Afterwards, the biomass pellets were suspended in 5 mL of extracting solution (CaCl$_2$ 0.1 M), stirred at 250 rpm, at room temperature for 4 hours with an orbital shaker, centrifuged (30 min, 12000×g, 15° C.), the supernatant (extract) recovered; the content (Lambert-Beer's law, molar absorption coefficient at 547 nm: $\varepsilon$=10.04 mL mg$^{-1}$ cm$^{-1}$) and the purity in B-PE (equation 4) were determined by spectrophotometric analysis (FIG. 9 and Table 6).

$$P=A_{547}/A_{280} \qquad \text{Equation (4):}$$

TABLE 6

% yield (Y) (mg/mg dry weight of the biomass) and purity of *P. cruentum* extracts obtained by applying the method of the invention.

| Sample | Cleaning solution | Extracting Solution | $Y_{B-PE}$ % | $P_{B-PE}$ |
|---|---|---|---|---|
| 1 | AS 1M | CaCl$_2$ | 1.61 | 3.48 |
| 2 | AS 1.5M | CaCl$_2$ | 2.28 | 3.38 |

EX. 7: Extraction of Phycobiliproteins (Phycocyanin and Allophycocyanin) from a Fresh (Wet) Biomass of *A. platensis* (*Spirulina*): Biomass/Extracting Solution Combination Ratio (AS 1M; CaCl$_2$ 0.1 M)

An aliquot of *A. platensis* cell culture was filtered using a nylon filter (mesh size=21 μm), to separate the biomass from the culture medium. The biomass was recovered from the filter using a spatula and was suspended in a small volume of cleaning solution (AS 1 M) in order to obtain a rather dense suspension.

5 mL of suspension in AS 1 M was filtered using a Whatman glass fibre filter (GF/C grade). The biomass was washed with deionised water on the same filter and the dry weight of the biomass was determined after drying at 105° C. for 4 hours.

Extraction/purification process according to the invention: the biomass suspension in AS 1 M was divided into 2 aliquots of 5 mL (Samples 1, 2), two 10 mL aliquots, (Sample 3 and 4), two 15 mL aliquots (Samples 5 and 6) and two 20 mL aliquots (Sample 7 and 8). AS 1 M was added to samples 1-6 in such a quantity as to obtain suspensions with the same final volume (20 mL).

The samples were sonicated sequentially for 2 minutes (power 100%, pulsation 0.6 s, sonotrode S2, Hielscher Ultrasonic Processor UP200S, 200 W, 24 kHz) in an ice/water bath. The sonication treatment was repeated a second time. Afterwards, the suspensions were stirred at room temperature at 250 rpm for 20 minutes with an orbital shaker, centrifuged (15 minutes, 12000×g, 15° C.) and the supernatant removed in each case.

Figure 10:
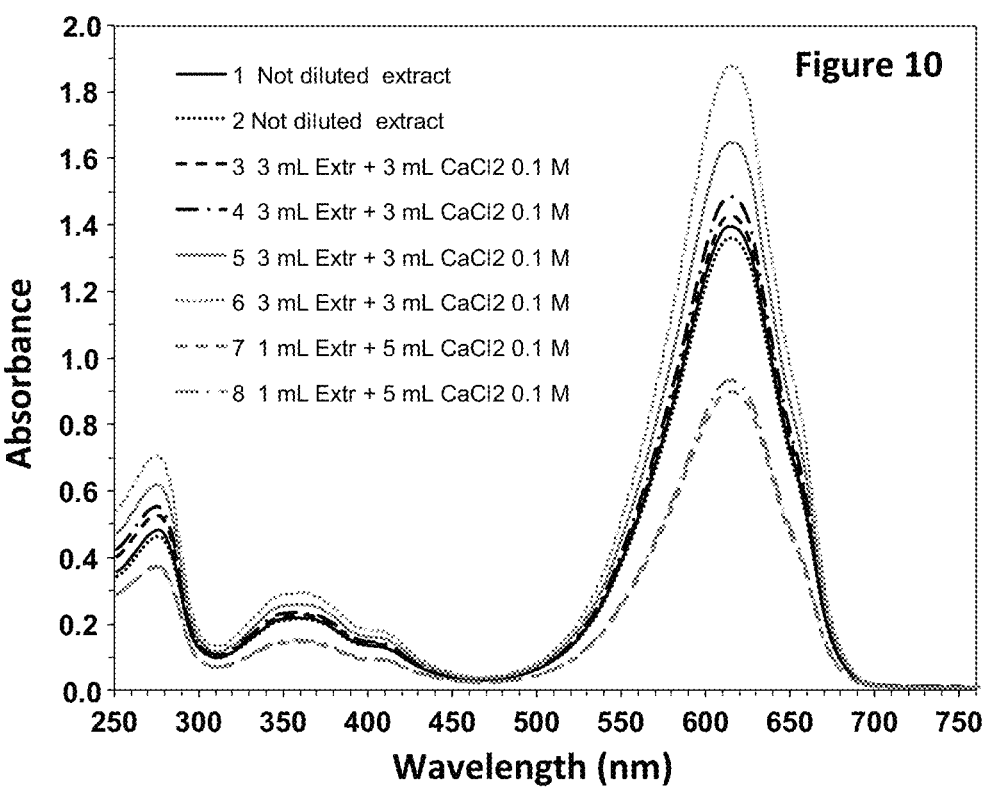
FIG. 10: Absorbance spectra of diluted solutions of *Spirulina* extracts obtained by applying the method of the invention, testing different biomass/extracting solution combination ratios ($CaCl_2$ 0.1 M). Some extracts were diluted to perform the spectrophotometric measurements (1—Not diluted extract; 2—Not diluted extract; 3-3 mL Extract+3 mL $CaCl_2$ 0.1 M; 4-3 mL Extract+3 mL $CaCl_2$ 0.1 M; 5-3 mL Extract+3 mL $CaCl_2$ 0.1 M; 6-3 mL Extract+3 mL $CaCl_2$ 0.1 M; 7-1 mL Extract+5 mL $CaCl_2$ 0.1 M; 8-1 mL Extract+5 mL $CaCl_2$ 0.1 M).

The pellets were suspended in 20 mL of 1 M AS solution and the cleaning/cell lysis process was repeated a second time (total sonication time 8 minutes). The biomass pellets were suspended in 10 mL of extracting solution (CaCl$_2$ 0.1 M), the suspensions stirred at room temperature at 250 rpm for 4 hours and 30 minutes with an orbital shaker, centrifuged (30 minutes, 12000×g, 15° C.), the supernatant (extract) recovered; the phycobiliprotein content and PC purity (FIG. 10 and Table 7) were determined by spectroscopic analysis (see Ex. 1).

TABLE 7

% yield (Y) (mg/mg dry weight (w.g.) of the biomass) and purity of Spirulina extracts obtained by applying the method of the invention. The concentration of phycobiliproteins (PC + APC) of the extracts and the volume ratio (mL) of the extracting solution/dry weight (g) of the biomass (R) are also reported.

| Sample | Cl. sol. | Extr. sol. | R (v/d.w.) | [PC + APC] (mg/mL) | $Y_{PC}$ % | $Y_{APC}$ % | $Y_{PC+APC}$ % | $P_{PC}$ |
|---|---|---|---|---|---|---|---|---|
| 1 | AS 1M | CaCl$_2$ 0.1M | 365 | 0.546 | 14.69 | 5.22 | 19.91 | 3.15 |
| 2 | AS 1M | CaCl$_2$ 0.1M | 365 | 0.531 | 14.39 | 5.13 | 19.52 | 3.20 |
| 3 | AS 1M | CaCl$_2$ 0.1M | 183 | 1.121 | 14.74 | 5.42 | 20.16 | 2.97 |
| 4 | AS 1M | CaCl$_2$ 0.1M | 183 | 1.164 | 15.26 | 5.59 | 20.85 | 2.95 |
| 5 | AS 1M | CaCl$_2$ 0.1M | 122 | 1.295 | 11.32 | 4.14 | 15.46 | 2.90 |
| 6 | AS 1M | CaCl$_2$ 0.1M | 122 | 1.475 | 12.99 | 4.71 | 17.70 | 2.90 |
| 7 | AS 1M | CaCl$_2$ 0.1M | 92 | 2.107 | 14.23 | 5.12 | 19.34 | 2.69 |
| 8 | AS 1M | CaCl$_2$ 0.1M | 92 | 2.185 | 14.90 | 5.36 | 20.26 | 2.75 |

EX. 8: Extraction of Phycobiliproteins (Phycocyanin and Allophycocyanin) from a Fresh (Wet) Biomass of *A. platensis* (*Spirulina*): Biomass/Extracting Solution Combination Ratio (AS 1.1 M; CaCl$_2$ 0.05 M)

An aliquot of *A. platensis* cell culture was filtered using a nylon filter (mesh size=21 μm), to separate the biomass from the culture medium. The biomass was recovered from the filter using a spatula and was suspended in a small volume of cleaning solution (AS 1.1 M) in order to obtain a rather dense suspension.

1 mL of the suspension in AS 1.1M was filtered using a Whatman glass fibre filter (GF/C grade). The biomass was washed with deionised water on the same filter and the weight of the dry biomass was determined after drying at 105° C. for 4 hours.

Extraction/purification process according to the invention: the biomass suspension in AS 1.1 M was divided into 2 aliquots of 3 mL (Samples 1, 2) and two further 20 mL aliquots, (Samples 3, 4). A volume of AS 1.1 M of 17 mL was added to samples 1 and 2 to achieve the same final volume as samples 3 and 4, resulting in suspensions of lower density than samples 3 and 4.

The samples were sonicated sequentially for 2 minutes (power 100%; pulsation 1 s—i.e., in continuous sonication; sonotrode S2; Hielscher Ultrasonic Processor UP200S; 200 W; 24 kHz) in an ice/water bath. The sonication treatment was repeated a second time. Afterwards, the suspensions were stirred at room temperature at 250 rpm for 20 minutes with an orbital shaker, centrifuged (15 minutes, 12000×g, 15° C.) and the supernatant removed.

Figure 11:
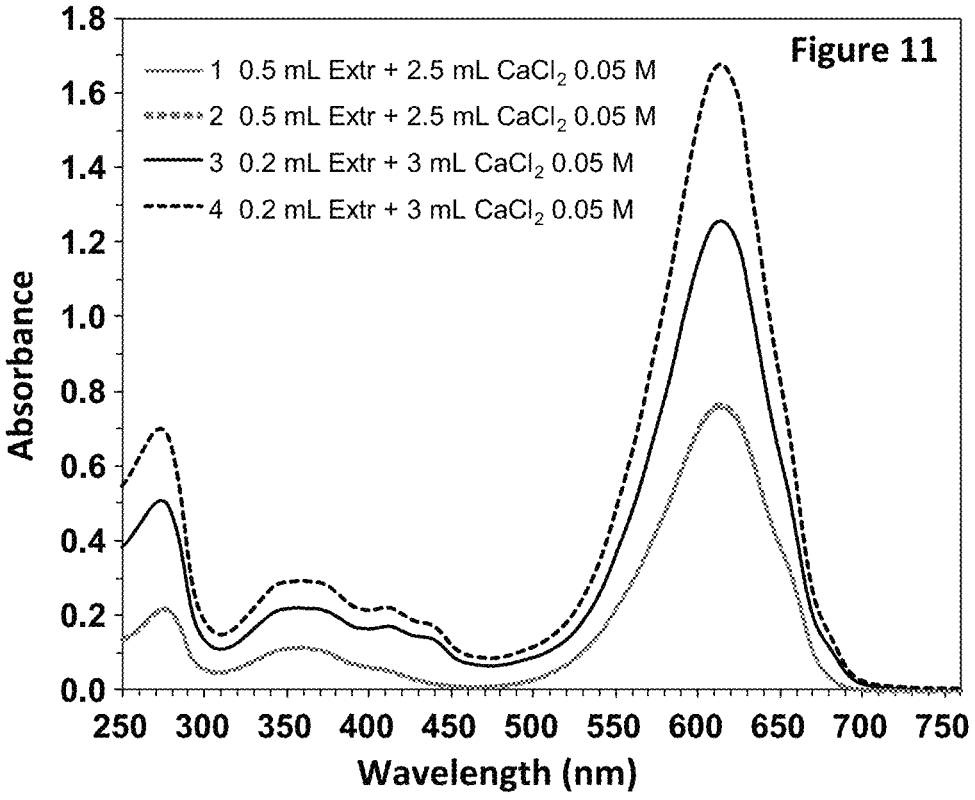
FIG. 11: Absorbance spectra of diluted solutions of *Spirulina* extracts obtained by applying the method of the invention, testing different biomass/extracting solution combination ratios ($CaCl_2$ 0.05 M). Some extracts were diluted to perform the spectrophotometric measurements (1-0.5 mL Extract+2.5 mL $CaCl_2$ 0.05 M; 2-0.5 mL Extract+2.5 mL $CaCl_2$ 0.05 M; 3-0.2 mL Extract+3 mL $CaCl_2$ 0.05 M; 4-0.2 mL Extract+3 mL $CaCl_2$ 0.05 M).

The pellets were suspended in 20 mL of 1.1 M AS solution and the cleaning/cell lysis process was repeated a second time (total sonication time 8 minutes). The biomass pellets were suspended in 10 mL of extracting solution (CaCl$_2$ 0.05M), the suspensions stirred at room temperature at 250 rpm for 4 hours and 30 minutes in an orbital shaker, centrifuged (30 minutes, 12000×g, 15° C.), the supernatant (extract) recovered; the phycobiliprotein content and PC purity (FIG. 11 and Table 8) were determined by spectroscopic analysis (see Es 1).

TABLE 8

% yield (Y) (mg/mg dry weight (w.g.) of the biomass) and purity of Spirulina extract obtained by applying the method of the invention. The concentration of phycobiliproteins (PC + APC) in the extract and the volume ratio of the extracting solution/dry weight of the biomass (R) are also reported.

| Pellets | Cl. sol. | Extr. sol. | R (v/d.w.) | [PC + APC] (mg/mL) | $Y_{PC}$ % | $Y_{APC}$ % | $Y_{PC+APC}$ % | $P_{PC}$ |
|---|---|---|---|---|---|---|---|---|
| 1 | AS 1.1M | CaCl$_2$ 0.05M | 296 | 0.901 | 19.41 | 7.19 | 26.59 | 3.60 |
| 2 | AS 1.1M | CaCl$_2$ 0.05M | 296 | 0.916 | 19.91 | 7.39 | 27.30 | 3.66 |
| 3 | AS 1.1M | CaCl$_2$ 0.05M | 45 | 3.957 | 12.78 | 4.52 | 17.30 | 2.64 |
| 4 | AS 1.1M | CaCl$_2$ 0.05M | 45 | 5.267 | 17.13 | 5.94 | 23.07 | 2.58 |

EX. 9: Extraction of Phycobiliproteins
(Phycocyanin and Allophycocyanin) from Fresh
(Wet) Biomass of *A. platensis* (*Spirulina*): Control
Experiment An aliquot of *A. platensis* cell culture was filtered using a nylon filter (mesh size=21 μm), to separate the biomass from the culture medium. The biomass was recovered from the filter using a spatula and was suspended in a small volume of deionised water in order to obtain a rather dense suspension.

0.5 mL of the suspension was filtered using a Whatman glass fibre filter (GF/C grade) and the weight of the dry biomass was determined after drying at 105° C. for 4 hours.

Extraction process: the biomass suspension was divided into 2 0.5 mL aliquots (samples 1, 2) and 6 8 mL aliquots (samples 3-8). A volume of 0.5 mL of $CaCl_2$ 1 M was added to each suspension, along with deionised water to have 10 mL suspensions, at a concentration of $CaCl_2$ equal to 0.05 M.

Figure 12:
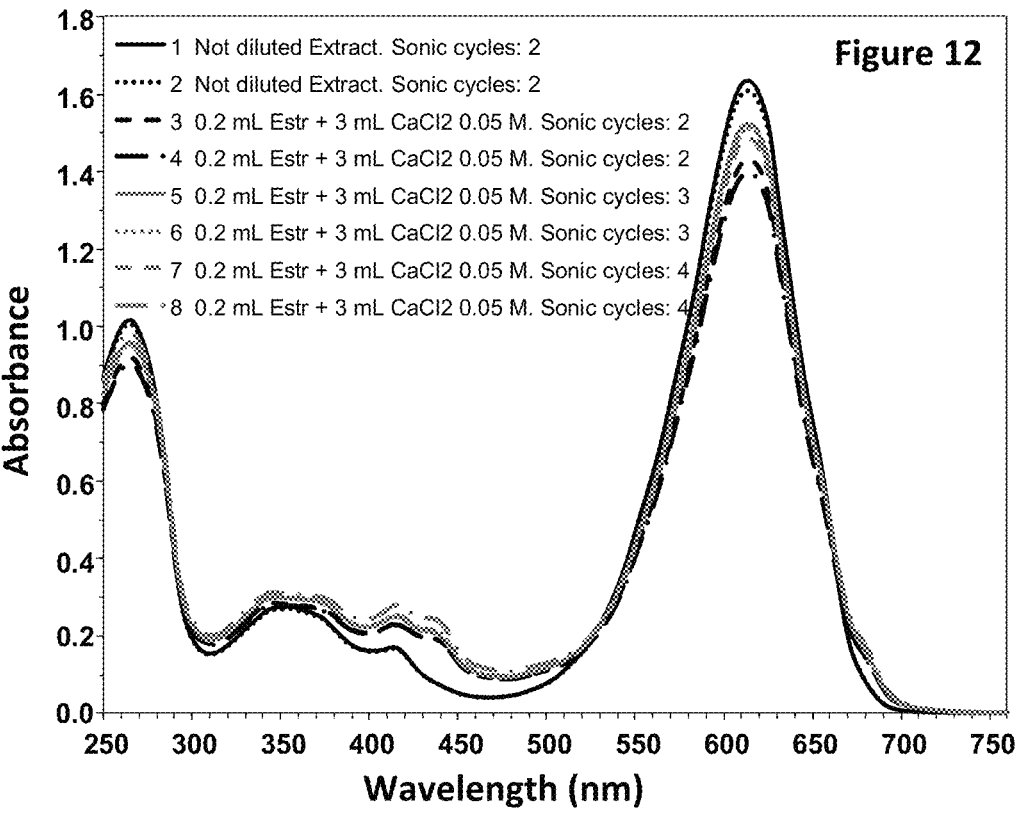
FIG. 12: Absorbance spectra of *Spirulina* extracts obtained by sonicating the biomass suspension without ammonium sulphate, directly in the extracting solution (control experiment). The extracts, if necessary, were diluted to perform the spectrophotometric measurements (1—Not diluted extract, 2 sonication cycles; 2—Not diluted extract, 2 sonication cycles; 3-0.2 mL Extract+3 mL $CaCl_2$ 0.05 M, 2 sonication cycles; 4-0.2 mL Extract+3 mL $CaCl_2$ 0.05 M, 2 sonication cycles; 5-0.2 mL Extract+3 mL $CaCl_2$ 0.05 M, 3 sonication cycles; 6-0.2 mL Extract+3 mL $CaCl_2$ 0.05 M, 3 sonication cycles; 7-0.2 mL Extract+3 mL $CaCl_2$ 0.05 M, 4 sonication cycles; 8-0.2 mL Extract+3 mL $CaCl_2$ 0.05 M, 4 sonication cycles).

The samples were sonicated sequentially for different times (several cycles of 2 minutes: power 100%; pulsation 1 s—i.e., in continuous sonication; sonotrode S2; Hielscher Ultrasonic Processor UP200S; 200 W; 24 kHz; in an ice/water bath), as shown in Table 9. After each sonication cycle (2 minutes per sonication cycle) the samples were kept in the ice/water bath for at least 1 minute. After sonication, the biomass suspensions in $CaCl_2$ 0.05 M were stirred at room temperature at 250 rpm for 5 hours in an orbital shaker, centrifuged (30 minutes, 12000×g, 15° C.), the supernatant (extract) recovered; the phycobiliprotein content and PC purity (FIG. 12 and Table 9) were determined by spectroscopic analysis (see Ex. 1).

TABLE 9

% yield (Y) (mg/mg dry weight (w.g.) of the biomass) and purity of Spirulina
extract obtained by applying the method of the invention. The concentration
of phycobiliproteins (PC + APC) in the extract and the volume ratio
of the extracting solution/weight of the dry biomass (R) are also reported.

| Sample | Extr. sol. | R (v/d.w.) | Son. cycles | [PC + APC] (mg/mL) | $Y_{PC}$ % | $Y_{APC}$ % | $Y_{PC+APC}$ % | $P_{PC}$ |
|--------|-----------|-----------|-------------|--------------------|----------|-----------|---------------|---------|
| 1 | $CaCl_2$ 0.05M | 763 | 2 | 0.317 | 18.39 | 5.65 | 24.04 | 2.02 |
| 2 | $CaCl_2$ 0.05M | 763 | 2 | 0.312 | 18.19 | 5.72 | 23.91 | 2.01 |
| 3 | $CaCl_2$ 0.05M | 49 | 2 | 4.457 | 14.93 | 4.71 | 19.64 | 1.90 |
| 4 | $CaCl_2$ 0.05M | 49 | 2 | 4.353 | 14.49 | 4.59 | 19.08 | 1.90 |
| 5 | $CaCl_2$ 0.05M | 49 | 3 | 4.739 | 15.81 | 5.05 | 20.86 | 1.94 |
| 6 | $CaCl_2$ 0.05M | 49 | 3 | 4.714 | 16.05 | 5.11 | 21.15 | 1.93 |
| 7 | $CaCl_2$ 0.05M | 49 | 4 | 4.631 | 15.86 | 5.10 | 20.96 | 1.91 |
| 8 | $CaCl_2$ 0.05M | 49 | 4 | 4.700 | 16.08 | 5.17 | 21.25 | 1.87 |

EX. 10: Extraction of Phycobiliproteins (Phycocyanin and Allophycocyanin) from a Fresh (Wet) Biomass of *A. platensis* (*Spirulina*): Variation of the Concentration of Ammonium Sulphate (AS) of the Cleaning Solution An aliquot of *A. platensis* cell culture was filtered using a nylon filter (mesh size=21 μm), to separate the biomass from the culture medium. The biomass was recovered from the filter using a spatula and was suspended in a small volume of AS 1 M in order to obtain a rather dense suspension.

1 mL of suspension in AS 1 M was filtered using a Whatman glass fibre filter (GF/C grade). The biomass was washed with deionised water on the same filter and the weight of the dry biomass was determined after drying at 105° C. for 4 hours and 30 minutes.

Extraction/purification process according to the invention: the biomass suspension in AS 1 M was divided into 12 aliquots of 4 mL. The appropriate volume of water and/or AS 3 M was added to each aliquot in order to obtain 6 mL of suspension having the desired concentration of AS.

The samples were sonicated sequentially for 2 minutes (power 100%; pulsation 0.6 s; sonotrode S2; Hielscher Ultrasonic Processor UP200S; 200 W; 24 kHz) in an ice/water bath. Afterwards, the suspensions were stirred at room temperature at 250 rpm for 20 minutes with an orbital shaker, centrifuged (15 minutes, 12000×g, 15° C.) and the supernatant removed.

The cleaning treatment was repeated a second time, after resuspending each pellet in 6 mL of cleaning solution of appropriate concentration of AS.

Figure 13:
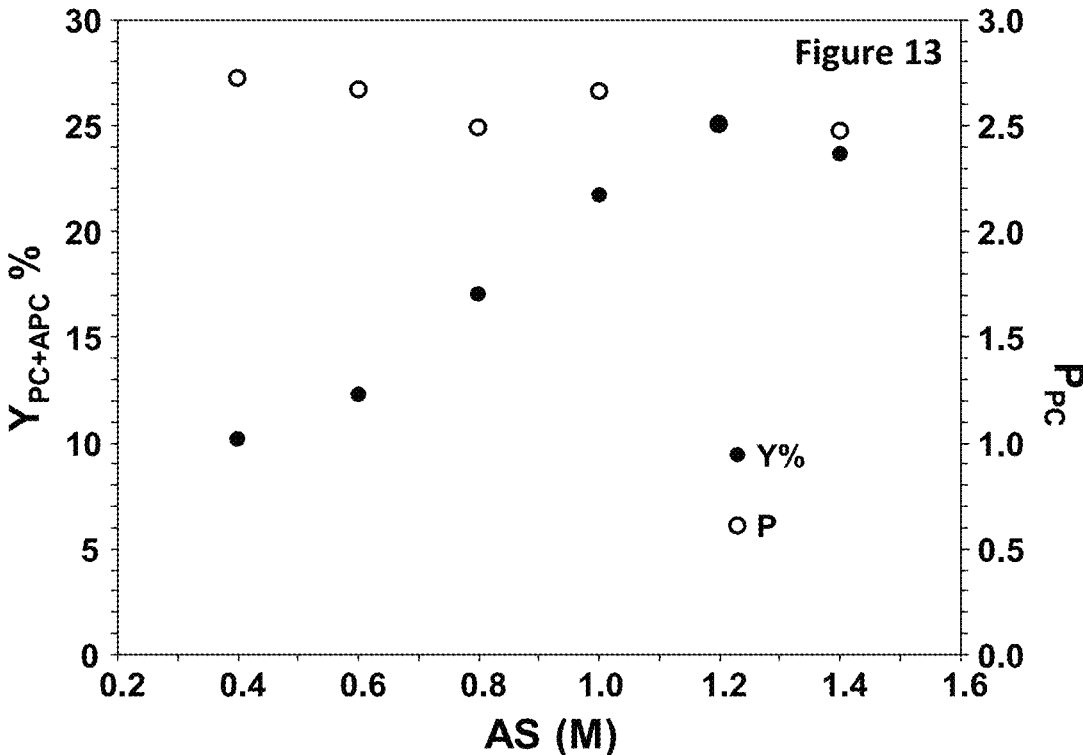

After the second cleaning cycle and the removal of the supernatant, the pellets were suspended in 5 mL of extracting solution (CaCl₂) 0.05 M), the suspensions stirred at room temperature at 250 rpm for 4 hours in an orbital shaker and centrifuged (30 minutes, 12000×g, 15° C.); the supernatant (extract) was recovered and the phycobiliprotein content and PC purity (FIG. 13 and Table 10) were determined by spectroscopic analysis (see Es 1).

the filter using a spatula and was suspended in a small volume of MilliQ ultrapure water in order to obtain a rather dense suspension.

1 mL of the suspension was filtered using a Whatman glass fibre filter (GF/C grade). The biomass was washed with MilliQ water on the same filter and the weight of the dry biomass was determined after drying at 105° C. for 4 hours and 30 minutes.

Extraction/purification process according to the invention: the biomass suspension was divided into 8 aliquots of 6.33 mL. A volume of 3.67 mL of AS 3 M was added to each aliquot, so as to have a final volume of 10 mL of suspension in AS 1.1 M (cleaning solution).

Each suspension was submitted to an initial sonication cycle (2 min, power 100%, pulsation 1 s (i.e., continuous sonication), sonotrode S2, Hielscher Ultrasonic Processor UP200S, 200 W, 24 kHz) in an ice/water bath. After the first sonication cycle, the suspensions were kept in an ice/water bath for at least 1 minute and were then submitted to a second sonication cycle. The suspensions were then kept under stirring at room temperature (28° C.) at 200 rpm for 10 min by means of an orbital shaker, then centrifuged (15 min, 12000×g, 25° C.) and the supernatant removed.

The process of cleaning/cell lysis was repeated a second time.

After that, the samples (biomass pellets) were suspended in 5 mL of extracting solution (Samples 1-2 in table sugar (sucrose) 0.1 M, Samples 3-4 in sorbitol 0.1 M, Samples 5-6 in Na-acetate buffer 0.1 M pH 5.1, Samples 7-8 in CaCl₂

TABLE 10

% yield (Y) (mg/mg dry weight of the biomass) and purity of Spirulina extract obtained by applying the method of the invention. The concentration of phycobiliproteins (PC + APC) in the extract is also reported.

| Pellets | Cl. sol. | Extr. sol. | [PC + APC] (mg/mL) | $Y_{PC}$ % | $Y_{APC}$ % | $Y_{PC+APC}$ % | $P_{PC}$ |
|---|---|---|---|---|---|---|---|
| 1 | AS 0.4M | CaCl₂ 0.1M | 0.7433 | 6.38 | 2.31 | 8.68 | 2.76 |
| 2 | AS 0.4M | CaCl₂ 0.1M | 0.9908 | 8.65 | 3.00 | 11.64 | 2.68 |
| 3 | AS 0.6M | CaCl₂ 0.1M | 1.0909 | 9.032 | 3.27 | 12.29 | 2.67 |
| 4 | AS 0.6M | CaCl₂ 0.1M | 1.0655 | 8.95 | 3.25 | 12.20 | 2.66 |
| 5 | AS 0.8M | CaCl₂ 0.1M | 1.3911 | 11.76 | 4.23 | 15.99 | 2.51 |
| 6 | AS 0.8M | CaCl₂ 0.1M | 1.5567 | 13.25 | 4.75 | 18.00 | 2.47 |
| 7 | AS 1.0M | CaCl₂ 0.1M | 1.9117 | 16.47 | 6.09 | 22.56 | 2.71 |
| 8 | AS 1.0M | CaCl₂ 0.1M | 1.7512 | 15.16 | 5.71 | 20.87 | 2.61 |
| 9 | AS 1.2M | CaCl₂ 0.1M | 2.2484 | 19.88 | 6.39 | 26.27 | 2.50 |
| 10 | AS 1.2M | CaCl₂ 0.1M | 2.0053 | 17.85 | 6.05 | 23.89 | 2.50 |
| 11 | AS 1.4M | CaCl₂ 0.1M | 1.9937 | 17.48 | 6.04 | 23.52 | 2.45 |
| 12 | AS 1.4M | CaCl₂ 0.1M | 1.9972 | 17.63 | 6.17 | 23.80 | 2.49 |

EX. 11: Extraction of Phycobiliproteins (Phycocyanin and Allophycocyanin) from a Fresh (Wet) Biomass of *A. platensis* (*Spirulina*): Comparison Between Different Extracting Solutions An aliquot of *A. platensis* cell culture was filtered using a nylon filter (mesh size=21 μm), to separate the biomass from the culture medium. The biomass was recovered from 0.05 M (control)), the suspensions stirred at room temperature (28° C.) at 200 rpm for 4 hours by means of an orbital shaker, centrifuged (20 min, 12000×g, 25° C.); the supernatant (extract) recovered, the phycobiliprotein content and PC purity (FIG. 14 and Table 11) determined by spectrophotometric analysis (see Ex. 1). The ratio of the volume of the extracting solution (expressed in mL) to the dry weight of the extracted biomass (expressed in g) is equal to 50.5.

TABLE 11

| | | [PC + APC] | | | | |
|---|---|---|---|---|---|---|
| Sample | Extracting solution | (mg/mL) | $Y_{PC}$ % | $Y_{APC}$ % | $Y_{PC+APC}$ % | $P_{PC}$ |
| 1 | Sucrose 0.1M | 4.3369 | 16.91 | 4.75 | 21.66 | 3.36 |
| 2 | Sucrose 0.1M | 4.2632 | 16.67 | 4.66 | 21.33 | 3.43 |
| 3 | Sorbitol 0.1M | 4.1431 | 16.43 | 4.67 | 21.10 | 3.44 |
| 4 | Sorbitol 0.1M | 4.2890 | 16.64 | 4.78 | 21.42 | 3.45 |
| 5 | Na—Ac 0.1M pH 5.1 | 2.8498 | 10.94 | 3.58 | 14.52 | 4.01 |
| 6 | Na—Ac 0.1M pH 5.1 | 2.9788 | 11.11 | 3.67 | 14.78 | 4.06 |
| 7 | CaCl$_2$ 0.05M | 4.1927 | 16.03 | 4.78 | 20.81 | 3.73 |
| 8 | CaCl$_2$ 0.05M | 4.1229 | 16.15 | 4.85 | 21.00 | 3.78 |

*% yield (Y) (mg/mg dry weight of the biomass) and purity of Spirulina extracts obtained by means of the method of the invention.*

EX. 12: Extraction of Phycobiliproteins (Phycocyanin and Allophycocyanin) from a Fresh (Wet) Biomass of *A. platensis* (*Spirulina*): Comparison Between Different Extracting Solutions An aliquot of *A. platensis* cell culture was filtered using a nylon filter (mesh size=21 μm), to separate the biomass from the culture medium. The biomass was recovered from the filter using a spatula and was suspended in a small volume of MilliQ ultrapure water in order to obtain a rather dense suspension.

1 mL of the suspension was filtered using a Whatman glass fibre filter (GF/C grade). The biomass was washed with MilliQ water on the same filter and the weight of the dry biomass was determined after drying at 105° C. for 4 hours and 30 minutes.

Extraction/purification process according to the invention: the biomass suspension was divided into 12 aliquots of 6.33 mL. A volume of 3.67 mL of AS 3 M was added to each aliquot, so as to have a final volume of 10 mL of suspension in AS 1.1 M (cleaning solution).

Each suspension was submitted to an initial sonication cycle (2 min, power 100%, pulsation 1 s (i.e., continuous sonication), sonotrode S2, Hielscher Ultrasonic Processor UP200S, 200 W, 24 kHz) in an ice/water bath. After the first sonication cycle, the suspensions were kept in an ice/water bath for at least 1 minute and were then submitted to a second sonication cycle. The suspensions were then kept under stirring at room temperature (23° C.) at 200 rpm for 10 min by means of an orbital shaker, then centrifuged (15 min, 12000×g, 20° C.) and the supernatant removed.

The process of cleaning/cell lysis was repeated a second time.

After that, the samples (biomass pellets) were suspended in 5 mL of extracting solution (Samples 1-2 in table sugar (sucrose) 0.1 M, Samples 3-4 in sorbitol 0.1 M, Samples 5-6 in Na-acetate buffer 0.1 M pH 5.5, Samples 7-8 in Na-acetate buffer 0.1 M pH 5.1, Samples 9-10 in CaCl$_2$) 0.1 M (control), Samples 11-12 in CaCl$_2$) 0.05 M (control)), stirred at room temperature (23° C.) at 200 rpm for 4 hours by means of an orbital shaker, centrifuged (20 min, 12000×g, 20° C.), the supernatant (extract) recovered, the phycobiliprotein content and PC purity (FIG. 15 and Table 12) determined by spectrophotometric analysis (see Ex. 1). The ratio of the volume of the extracting solution (expressed in mL) to the dry weight of the extracted biomass (expressed in g) is equal to 54.6.

TABLE 12

| | | [PC + APC] | | | | |
|---|---|---|---|---|---|---|
| Sample | Extracting solution | (mg/mL) | $Y_{PC}$ % | $Y_{APC}$ % | $Y_{PC+APC}$ % | $P_{PC}$ |
| 1 | Sucrose 0.1M | 3.9719 | 16.87 | 4.80 | 21.67 | 3.22 |
| 2 | Sucrose 0.1M | 4.0587 | 17.36 | 4.96 | 22.32 | 3.24 |
| 3 | Sorbitol 0.1M | 4.0323 | 17.15 | 4.89 | 22.04 | 3.39 |
| 4 | Sorbitol 0.1M | 3.9841 | 17.43 | 5.00 | 22.43 | 3.33 |
| 5 | Na—Ac 0.1M pH 5.5 | 1.9494 | 7.96 | 2.63 | 10.59 | 3.61 |
| 6 | Na—Ac 0.1M pH 5.5 | 2.1055 | 8.69 | 2.89 | 11.58 | 3.60 |
| 7 | Na—Ac 0.1M pH 5.1 | 2.0343 | 8.42 | 2.66 | 11.08 | 3.83 |
| 8 | Na—Ac 0.1M pH 5.1 | 2.0420 | 8.66 | 2.70 | 11.36 | 3.91 |
| 9 | CaCl$_2$ 0.1M | 4.0877 | 17.46 | 5.29 | 22.75 | 2.55 |
| 10 | CaCl$_2$ 0.1M | 4.2327 | 17.92 | 5.45 | 23.37 | 2.56 |
| 11 | CaCl$_2$ 0.05M | 3.0645 | 17.13 | 5.17 | 22.30 | 3.17 |
| 12 | CaCl$_2$ 0.05M | 4.0046 | 17.02 | 5.22 | 22.24 | 3.23 |

*% yield (Y) (mg/mg dry weight of the biomass) and purity of Spirulina extracts obtained by means of the method of the invention.*

EX. 13: Extraction of B-Phycoerythrin (B-PE) from a Fresh (Wet) Biomass of *Porphyridium cruentum*: Solvents and Extraction Time A 10 mL aliquot of *Porphyridium cruentum* culture was filtered using a Whatman glass fibre filter (GF/C grade). The biomass was washed with MilliQ water on the same filter and the weight of the dry biomass was determined after drying at 105° C. for 4 hours and 30 minutes.

Extraction/purification process according to the invention: 4 aliquots (40 mL) of *Porphyridium cruentum* culture were placed in centrifuge tubes, centrifuged (12000×g, 10 min, 18° C.) and the culture medium (supernatant) removed.

The biomass pellets were submitted to the method of the invention: the samples were suspended in 10 mL of cleaning solution (AS 1.5 M), each suspension was submitted to a first cycle of sonication (2 min, power 100%, pulsation 1 s (i.e., continuous sonication), sonotrode S2, Hielscher Ultrasonic Processor UP200S, 200 W, 24 kHz) in an ice/water bath. After the first sonication cycle, the suspensions were kept in an ice/water bath for at least 1 minute and were then submitted to a second sonication cycle. The suspensions were then kept under stirring at room temperature (29° C.) at 200 rpm for 15 min by means of an orbital shaker, then centrifuged (10 min, 12000×g, 18° C.) and the supernatant removed.

The process of cleaning/cell lysis was repeated a second time.

Subsequently, the samples (biomass pellets) were suspended in 5 mL of extracting solution (NaCl 0.1 M: samples 1 and 3; CaCl$_2$ 0.1 M: samples 2 and 4) for 5 hours (samples 1 and 2) or 24 hours (samples 3 and 4). At the end of the extraction period, the suspensions were centrifuged (30 min, 12000×g, 18° C.), the supernatant (extract) recovered; the content and purity of B-PE (FIG. 16 and Table 13) were determined by spectrophotometric analysis (see Ex. 6).

Figure 16:
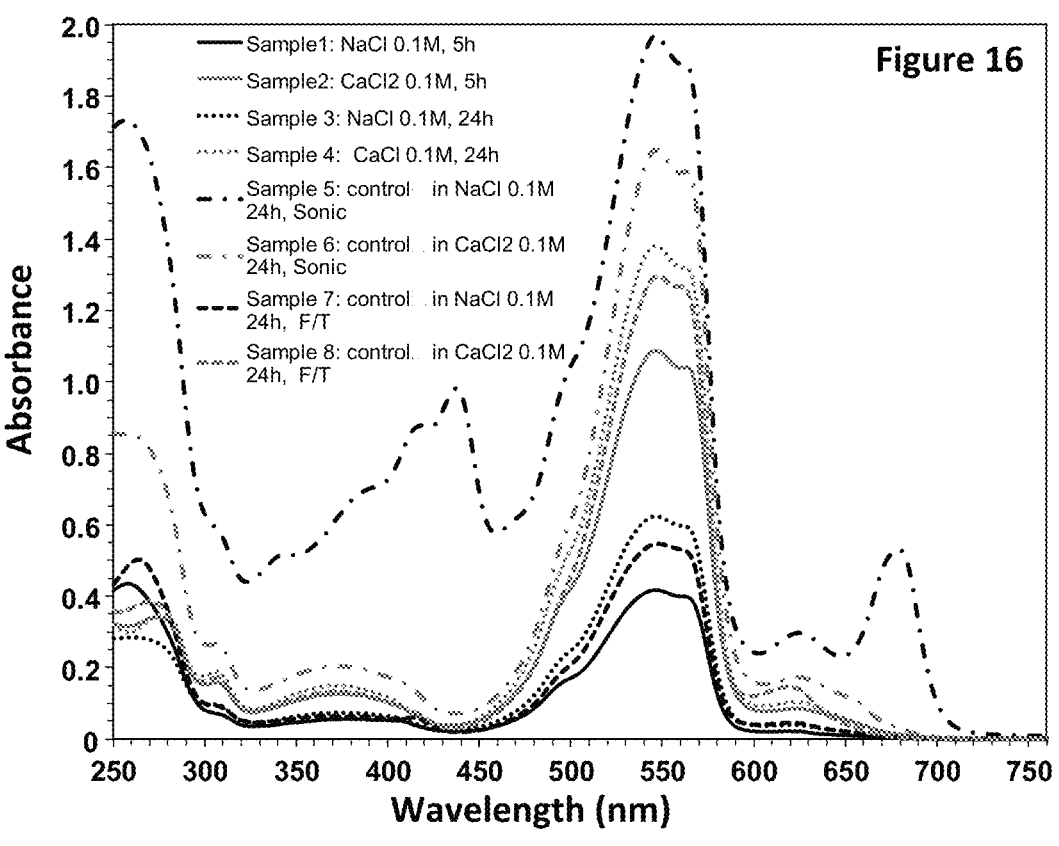
FIG. 16: Absorbance spectra of diluted solutions of *P. cruentum* extracts (fresh mass) obtained by applying the method of the invention, using two different extracting solvents, NaCl 0.1 M (Samples 1 and 3) and $CaCl_2$ 0.1 M (Samples 2 and 4) and extracting for different times, 5 hours (Samples 1 and 2) and 24 hours (Samples 3 and 4). Spectra of control extracts obtained by sonicating the biomass directly in the extracting solution (Samples 5 and 6) or by breaking down the cells by freezing/thawing (F/T) (Samples 7 and 8) are also shown.

Control tests: 4 aliquots (40 mL) of *Porphyridium cruentum* culture (samples 5-8) were placed in centrifuge tubes, centrifuged (12000×g, 10 min, 18° C.) and the culture medium (supernatant) removed. The extraction was carried out by subjecting the sample to freeze/thawing cycles (Freeze-Thawing, F/T, 3 of them were performed (between −20° C. (2 hours) and about 25° C.)) or to sonication directly in the extracting solvent (FIG. 16 and Table 13).

TABLE 13

% yield (Y) (mg/mg dry weight of the biomass) and purity of *P. cruentum* extracts obtained both by applying the method of the invention (1-4) and conventional methods (5-8).

| Sample | Cleaning solution | Cell disruption/ Extraction | Extracting solvent | t (hours)/ Extraction | $Y_{B-PE}$ % | $P_{B-PE}$ |
|---|---|---|---|---|---|---|
| 1 | AS 1.5M | Sonication | NaCl 0.1M | 5 | 1.64 | 1.42 |
| 2 | AS 1.5M | Sonication | CaCl$_2$ 0.1M | 5 | 4.20 | 3.32 |
| 3 | AS 1.5M | Sonication | NaCl 0.1M | 24 | 2.50 | 2.56 |
| 4 | AS 1.5M | Sonication | CaCl$_2$ 0.1M | 24 | 5.65 | 4.01 |
| 5 | No | Sonication | NaCl 0.1M | 24 | 8.22* | 1.45 |
| 6 | No | Sonication | CaCl$_2$ 0.1M | 24 | 6.95 | 2.44 |
| 7 | No | F/T | NaCl 0.1M | 24 | 3.02 | 1.55 |
| 8 | No | F/T | CaCl$_2$ 0.1M | 24 | 7.01 | 3.70 |

*B-PE yield is overestimated due to the high content of carotenoids and chlorophyll present in the extract (see FIG. 16).

EX. 14: Extraction of B-Phycoerythrin (B-PE) from a Dried Biomass of *Porphyridium cruentum*: Extraction Temperature and Time Freeze-dried biomass samples of *Porphyridium cruentum* (about 50 mg each) were submitted to the method of the invention: the samples were suspended in 10 mL of cleaning solution (AS 1.5 M), each suspension was submitted to a first cycle of sonication (2 min, power 100%, pulsation 1 s (i.e., continuous sonication), sonotrode S2, Hielscher Ultrasonic Processor UP200S, 200 W, 24 kHz) in an ice/water bath. After the first sonication cycle, the suspensions were kept in an ice/water bath for at least 1 minute and were then submitted to a second sonication cycle. The suspensions were then kept under stirring at room temperature (23° C.) at 200 rpm for 15 min by means of an orbital shaker, then centrifuged (10 min, 12000×g, 20° C.) and the supernatant removed.

The process of cleaning/cell lysis was repeated a second time.

Afterwards, the samples (biomass pellets) were suspended in 5 mL of extracting solution (CaCl$_2$ 0.1 M) and extracted by applying the conditions (extraction temperature and time) reported in Table 12. At the end of the extraction period, the suspensions were centrifuged (30 min, 12000×g, 15° C.), the supernatant (extract) recovered; the content and purity of B-PE were determined by spectrophotometric analysis (see Ex. 6).

Figure 17:
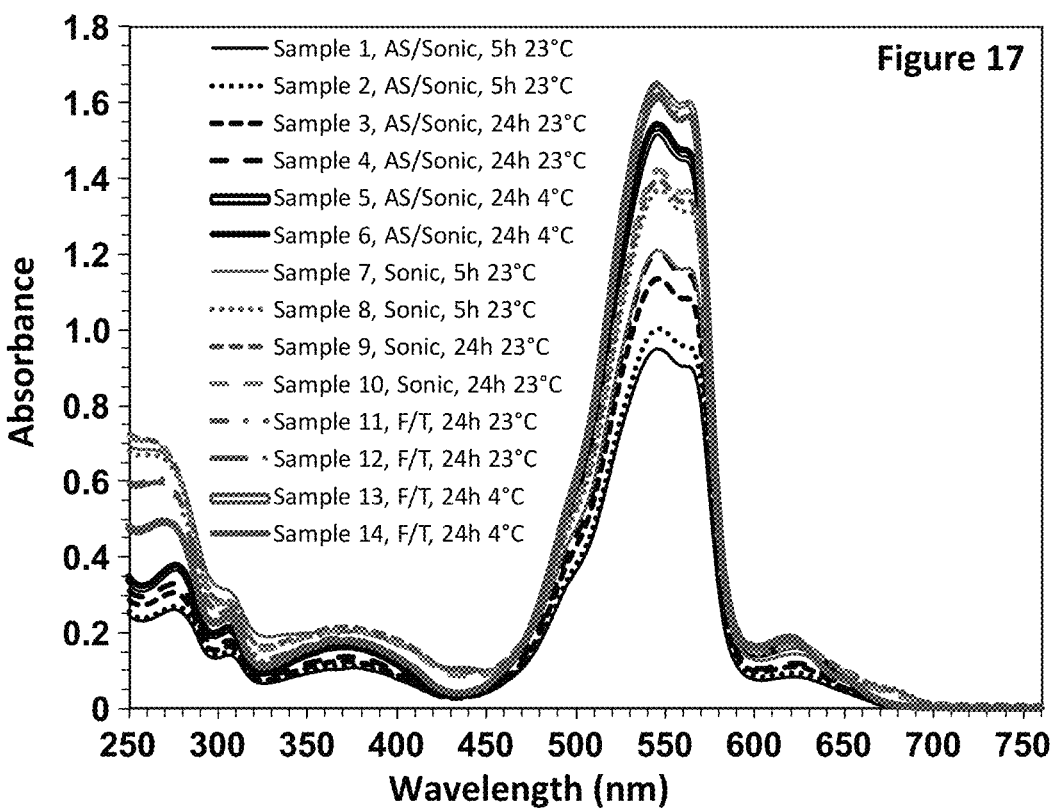
FIG. 17: Absorbance spectra of diluted solutions of *P. cruentum* extracts (freeze-dried) obtained by applying the method of the invention, at two different temperatures, 23° C. (Samples 1-4) and 4° C. (Samples 5-6) and for different times, 5 hours (Samples 1-2) and 24 hours (Samples 3-6). Spectra of control extracts obtained by sonicating the biomass directly in the extracting solution ($CaCl_2$ 0.1 M) (Samples 7-10) or by breaking down the cells by freezing/thawing (F/T) (Samples 11-14) are also shown.
Figure 17:
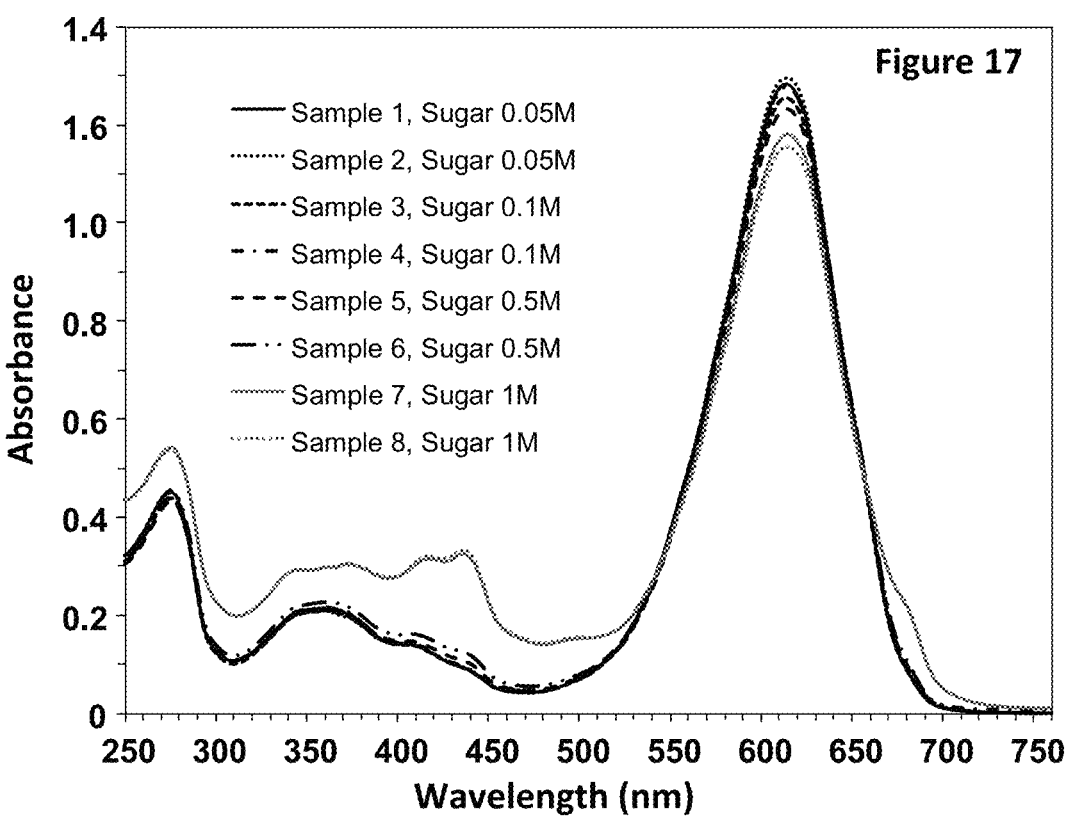

Control tests were performed on samples of similar mass (about 50 mg), which were extracted after subjecting the sample either to freeze-thawing cycles (Freeze-Thawing, F/T, 3 of them were performed (between −20° C. (2 hours) and about 25° C.)) or to sonication directly performed in the extracting solvent, 5 mL of CaCl$_2$ 0.1 M (FIG. 17 and Table 14).

TABLE 14

% yield (Y) (mg/mg dry weight of the biomass) and purity of *P. cruentum* extracts obtained by applying the method of the invention.

| Sample | Cleaning solution | Cell disruption/ Extraction | T (° C.)/ Extraction | t (hours)/ Extraction | $Y_{B-PE}$ % | $P_{B-PE}$ |
|---|---|---|---|---|---|---|
| 1 | AS 1.5M | Sonication | 23 | 5 | 5.48 | 3.77 |
| 2 | AS 1.5M | Sonication | 23 | 5 | 5.72 | 3.85 |
| 3 | AS 1.5M | Sonication | 23 | 24 | 6.77 | 3.86 |
| 4 | AS 1.5M | Sonication | 23 | 24 | 7.04 | 3.83 |
| 5 | AS 1.5M | Sonication | 4 | 24 | 8.99 | 4.23 |
| 6 | AS 1.5M | Sonication | 4 | 24 | 9.11 | 4.20 |
| 7 | No | Sonication | 23 | 5 | 6.69 | 2.05 |
| 8 | No | Sonication | 23 | 5 | 7.79 | 2.39 |
| 9 | No | Sonication | 23 | 24 | 8.11 | 2.41 |
| 10 | No | Sonication | 23 | 24 | 8.23 | 2.47 |
| 11 | No | F/T | 23 | 24 | 8.72 | 3.08 |
| 12 | No | F/T | 23 | 24 | 9.39 | 3.22 |
| 13 | No | F/T | 4 | 24 | 9.19 | 3.66 |
| 14 | No | F/T | 4 | 24 | 8.96 | 3.59 |

EX. 15: Extraction of Phycobiliproteins (Phycocyanin and Allophycocyanin) from a Fresh (Wet) Biomass of *A. platensis* (*Spirulina*): Effect of the Concentration of Table Sugar (Sucrose, Disaccharide) in the Extracting Solution An aliquot of *A. platensis* cell culture was filtered using a nylon filter (mesh size=21 μm), to separate the biomass from the culture medium. The biomass was recovered from the filter using a spatula and was suspended in a small volume of MilliQ ultrapure water in order to obtain a rather dense suspension.

2 mL of the suspension was filtered using a Whatman glass fibre filter (GF/C grade). The biomass was washed with MilliQ water on the same filter and the weight of the dry biomass was determined after drying at 105° C. for 5 hours.

Extraction/purification process according to the invention: the biomass suspension was divided into 10 aliquots of 5.7 mL. A volume of 3.3 mL of AS 3 M was added to each aliquot, so as to have a final volume of 9 mL of suspension in AS 1.1 M (cleaning solution).

Each suspension was submitted to an initial sonication cycle (2 min, power 100%, pulsation 1 s (i.e., continuous sonication), sonotrode S2, Hielscher Ultrasonic Processor UP200S, 200 W, 24 kHz) in an ice/water bath. After the first sonication cycle, the suspensions were kept in an ice/water bath for at least 1 minute and were then submitted to a second sonication cycle. The suspensions were then kept under stirring at room temperature (24° C.) at 250 rpm for 10 min by means of an orbital shaker, then centrifuged (15 min, 12000×g, 20° C.) and the supernatant removed.

The process of cleaning/cell lysis was repeated a second time.

After that, the samples (biomass pellets) were suspended in 3 mL of extracting solution (Samples 1-2 in sugar 0.05 M, Samples 3-4 in sugar 0.1 M, Samples 5-6 in sugar 0.5 M, Samples 7-8 in sugar 1 M, Samples 9-10 in sugar 60%), stirred at room temperature (23° C.) at 250 rpm for 4 hours by means of an orbital shaker, centrifuged (30 min, 12000×g, 20° C.), the supernatant (extract) recovered, the phycobiliprotein content and PC purity (FIG. 18 and Table 15) determined by spectrophotometric analysis (see Ex. 1). The ratio of the volume of the extracting solution (expressed in mL) to the dry weight of the extracted biomass (expressed in g) is equal to 61.9.

the filter using a spatula and was suspended in a small volume of MilliQ ultrapure water in order to obtain a rather dense suspension.

2 mL of the suspension was filtered using a Whatman glass fibre filter (GF/C grade). The biomass was washed with MilliQ water on the same filter and the weight of the dry biomass was determined after drying at 105° C. for 5 hours.

Extraction/purification process according to the invention: the biomass suspension was divided into 10 aliquots of 5.7 mL. A volume of 3.3 mL of AS 3 M was added to each aliquot, so as to have a final volume of 9 mL of suspension in AS 1.1 M (cleaning solution).

Each suspension was submitted to an initial sonication cycle (2 min, power 100%, pulsation 1 s (i.e., continuous sonication), sonotrode S2, Hielscher Ultrasonic Processor UP200S, 200 W, 24 kHz) in an ice/water bath. After the first sonication cycle, the suspensions were kept in an ice/water bath for at least 1 minute and were then submitted to a second sonication cycle. The suspensions were then kept under stirring at room temperature (23° C.) at 250 rpm for 10 min by means of an orbital shaker, then centrifuged (15 min, 12000×g, 20° C.) and the supernatant removed.

The process of cleaning/cell lysis was repeated a second time.

After that, the samples (biomass pellets) were suspended in 3 mL of extracting solution (Samples 1-2 in sorbitol 0.05 M, Samples 3-4 in sorbitol 0.1 M, Samples 5-6 in sorbitol 0.5 M, Samples 7-8 in sorbitol 1 M, Sample 9 in sorbitol

TABLE 15

% yield (Y) (mg/mg dry weight of the biomass) and purity of Spirulina extracts obtained by means of the method of the invention.

| Sample | Extracting solution | [PC + APC] (mg/mL) | $Y_{PC}$ % | $Y_{APC}$ % | $Y_{PC+APC}$ % | $P_{PC}$ |
|---|---|---|---|---|---|---|
| 1 | Sugar 0.05M | 3.3831 | 16.93 | 5.66 | 22.59 | 3.06 |
| 2 | Sugar 0.05M | 3.4252 | 17.55 | 5.95 | 23.49 | 3.07 |
| 3 | Sugar 0.1M | 3.3134 | 17.28 | 5.82 | 23.10 | 3.07 |
| 4 | Sugar 0.1M | 3.3725 | 17.16 | 5.82 | 22.98 | 3.15 |
| 5 | Sugar 0.5M | 3.2749 | 16.35 | 5.82 | 22.17 | 3.08 |
| 6 | Sugar 0.5M | 3.3834 | 17.09 | 5.97 | 23.05 | 3.03 |
| 7 | Sugar 1M | 3.1171 | 15.38 | 5.57 | 20.96 | 2.37 |
| 8 | Sugar 1M | 3.0551 | 15.54 | 5.69 | 21.23 | 2.34 |
| 9 | Sugar 60% | * | * | * | * | * |
| 10 | Sugar 60% | * | * | * | * | * |

\* The purity and concentration (and therefore the yield) of phycocyanin and allophycocyanin in the extract were not determined, as it was not possible to separate it from the biomass by centrifugation, probably due to the high viscosity of the suspension.

Figure 19:
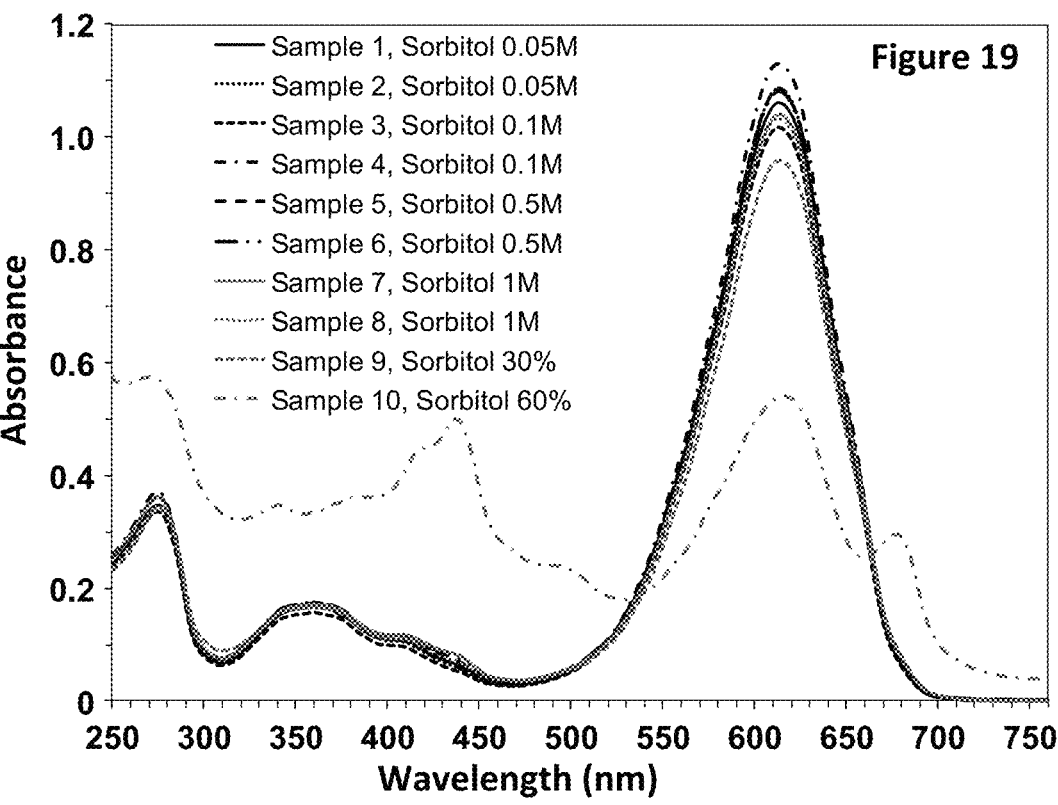
FIG. 19: Absorbance spectra of diluted solutions of *Spirulina* extracts obtained by applying the method of the invention, using different concentrations of sorbitol in the extracting solution. The extracts were diluted to perform the spectrophotometric measurements (Samples 1 and 2: sorbitol 0.05 M; Samples 3 and 4: sorbitol 0.1 M; Samples 5 and 6: sorbitol 0.5 M; Samples 7 and 8: sorbitol 1 M, Sample 9: sorbitol 30%; Sample 10: sorbitol 60%).

EX. 16: Extraction of Phycobiliproteins (Phycocyanin and Allophycocyanin) from a Fresh (Wet) Biomass of *A. platensis* (*Spirulina*): Effect of the Sorbitol (Polyol) Concentration in the Extracting Solution An aliquot of *A. platensis* cell culture was filtered using a nylon filter (mesh size=21 µm), to separate the biomass from the culture medium. The biomass was recovered from 30%, Sample 10 in sorbitol 60%), stirred at room temperature (23° C.) at 250 rpm for 4 hours by means of an orbital shaker, centrifuged (30 min, 12000×g, 20° C.), the supernatant (extract) recovered, the phycobiliprotein content and PC purity (FIG. 19 and Table 16) determined by spectrophotometric analysis (see Ex. 1). The ratio of the volume of the extracting solution (expressed in mL) to the dry weight of the extracted biomass (expressed in g) is equal to 61.9.

TABLE 16

| | | [PC + APC] | | | | |
|---|---|---|---|---|---|---|
| Sample | Extracting solution | (mg/mL) | $Y_{PC}$ % | $Y_{APC}$ % | $Y_{PC+APC}$ % | $P_{PC}$ |
| 1 | Sorbitol 0.05M | 2.7788 | 13.23 | 4.26 | 17.49 | 3.28 |
| 2 | Sorbitol 0.05M | 2.8479 | 13.36 | 4.27 | 17.63 | 3.22 |
| 3 | Sorbitol 0.1M | 2.6649 | 12.78 | 4.16 | 16.94 | 3.25 |
| 4 | Sorbitol 0.1M | 2.9672 | 13.82 | 4.55 | 18.37 | 3.25 |
| 5 | Sorbitol 0.5M | 2.8630 | 14.16 | 4.75 | 18.91 | 3.18 |
| 6 | Sorbitol 0.5M | 2.8514 | 13.13 | 4.41 | 17.54 | 3.20 |
| 7 | Sorbitol 1M | 2.7544 | 12.53 | 4.36 | 16.88 | 3.07 |
| 8 | Sorbitol 1M | 2.7396 | 12.79 | 4.52 | 17.30 | 3.18 |
| 9 | Sorbitol 30% | 2.5350 | 11.93 | 4.13 | 16.06 | 2.92 |
| 10 | Sorbitol 60% | * | * | * | * | 0.98 |

% yield (Y) (mg/mg dry weight of the biomass) and purity of Spirulina extracts obtained by means of the method of the invention.

* It is not possible to determine the concentration (and therefore the yield) of phycocyanin and allophycocyanin spectrophotometrically due to interference of the other pigments present in the extract, which is green in colour.

Figure 20:
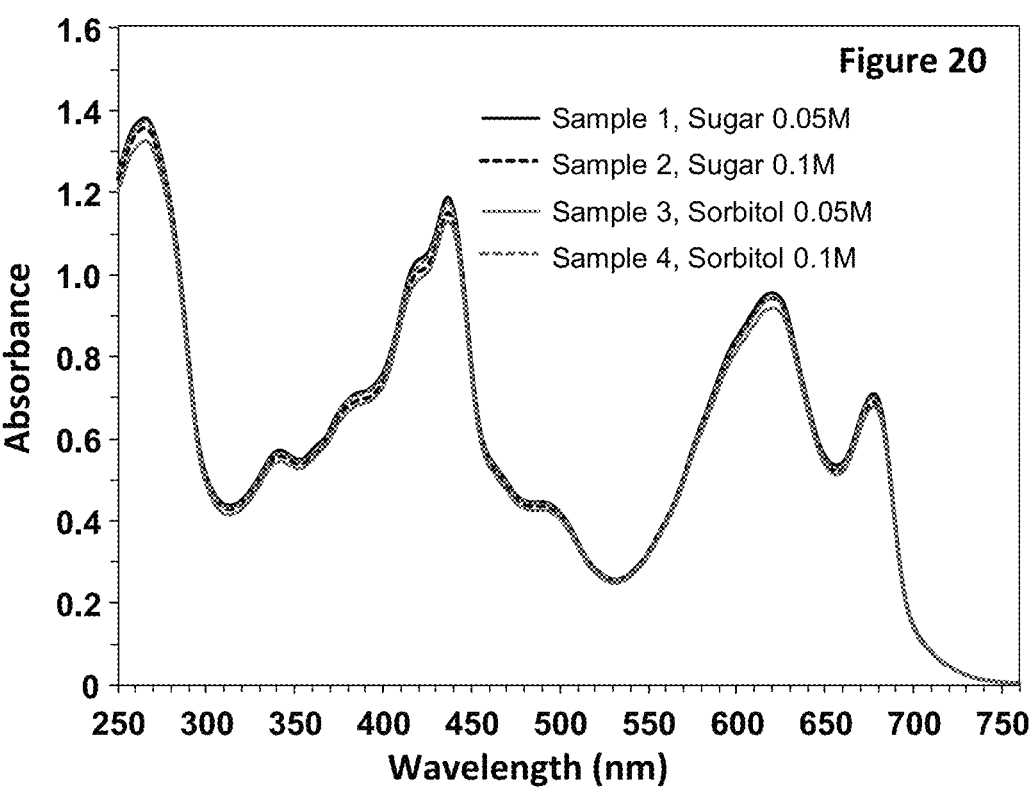
FIG. 20: Absorbance spectra of diluted solutions of *Spirulina* extracts obtained by sonicating the biomass suspension without ammonium sulphate, directly in the extracting solution (control experiment). The extracts were diluted to perform the spectrophotometric measurements (Sample 1: table sugar 0.05 M; Sample 2: table sugar 0.1 M; Sample 3: sorbitol 0.05 M; Sample 3: sorbitol 0.1 M). The solutions are green in colour due to the strong contamination by chlorophyll.

EX. 17: Extraction of Phycobiliproteins (Phycocyanin and Allophycocyanin) from a Fresh (Wet) Biomass of *A. platensis* (*Spirulina*) by Sonication (Directly in the Extracting Solution: Table Sugar and Sorbitol): Control Tests An aliquot of *A. platensis* cell culture was filtered using a nylon filter (mesh size=21 μm), to separate the biomass from the culture medium. The biomass was recovered from After that, the samples were kept under stirring at room temperature (24° C.) at 250 rpm for 4 hours by means of an orbital shaker, centrifuged (30 min, 12000×g, 20° C.) and the supernatant (extract) recovered for the determination of phycobiliprotein content and PC purity. However, the concentration (and therefore the yield) of phycocyanin and allophycocyanin could not be determined spectrophotometrically due to the interference of the other pigments present in the extract, which is green in colour (FIG. 20 and Table 17).

TABLE 17

| | | [PC + APC] | | | | |
|---|---|---|---|---|---|---|
| Sample | Extracting solution | (mg/mL) | $Y_{PC}$ % | $Y_{APC}$ % | $Y_{PC+APC}$ % | $P_{PC}$ |
| 1 | Sugar 0.05M | * | * | * | * | 0.80 |
| 2 | Sugar 0.1M | * | * | * | * | 0.81 |
| 3 | Sorbitol 0.05M | * | * | * | * | 0.80 |
| 4 | Sorbitol 0.1M | * | * | * | * | 0.80 |

% yield (Y) (mg/mg dry weight of the biomass) and purity of Spirulina extracts obtained by means of the method of the invention.

* It is not possible to determine the concentration (and therefore the yield) of phycocyanin and allophycocyanin spectrophotometrically due to interference of the other pigments present in the extract, which is green in colour.

the filter using a spatula and was suspended in a small volume of MilliQ ultrapure water in order to obtain a rather dense suspension.

3 mL of the suspension was filtered using a Whatman glass fibre filter (GF/C grade). The biomass was washed with MilliQ water on the same filter and the weight of the dry biomass was determined after drying at 105° C. for 5 hours.

Extraction process: the biomass suspension was divided into 4 aliquots of 8.1 mL. A volume of 0.45 mL (Samples 1 and 3) or 0.9 mL (Samples 2 and 4) of table sugar (sucrose, monosaccharide) or sorbitol 1 M was added to each aliquot in order to have a final volume of 9 mL of suspension in sugar or sorbitol (polyol) 0.05 M and 0.1 M, respectively. Samples 1 and 3 were brought up to volume by adding 0.45 mL of MilliQ ultrapure water.

Each sample was submitted to 4 sonication cycles of 2 minutes (power 100%, 1 s pulsation (i.e. continuous sonication), sonotrode S2, Hielscher Ultrasonic Processor UP200S, 200 W, 24 kHz) in an ice/water bath. Between one sonication cycle and the next, the samples were kept in an ice and water bath for at least 1 minute.

EX. 18: Extraction of B-Phycoerythrin (B-PE) from a Freeze-Dried and Ground Biomass of *Porphyridium cruentum*: Solvents, Extraction Temperature and Time Freeze-dried biomass samples of *Porphyridium cruentum* (about 50 mg each) were submitted to the method of the invention: the samples were suspended in 10 mL of cleaning solution (AS 1.5 M), each suspension was submitted to a first cycle of sonication (2 min, power 100%, pulsation 1 s (i.e., continuous sonication), sonotrode S2, Hielscher Ultrasonic Processor UP200S, 200 W, 24 kHz) in an ice/water bath.

After the first sonication cycle, the suspensions were kept in an ice/water bath for at least 1 minute and were then submitted to a second sonication cycle. The suspensions were then kept under stirring at room temperature (23° C.) at 200 rpm for 10 min by means of an orbital shaker, then centrifuged (10 min, 12000×g, 20° C.) and the supernatant removed.

The process of cleaning/cell lysis was repeated a second time.

Figure 21:
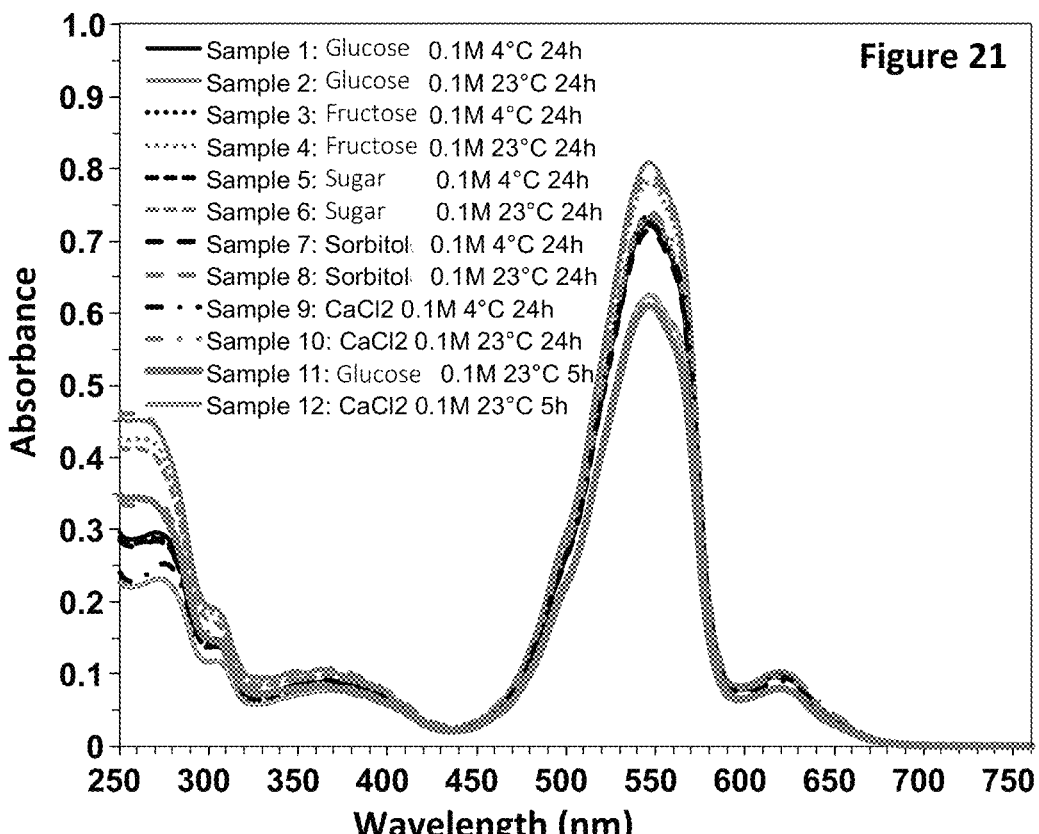
FIG. 21: Absorbance spectra of diluted solutions of *P. cruentum* extracts (lyophilized) obtained by applying the method of the invention, using different extracting solutions and by applying two different extraction temperatures (Samples 1 and 2: glucose 0.1 M, maintained at 4° C. and 23° C., respectively; Samples 3 and 4: fructose 0.1 M, maintained at 4° C. and 23° C., respectively; Samples 5 and 6: table sugar (sucrose) 0.1 M, maintained at 4° C. and 23° C., respectively; Samples 7 and 8: sorbitol 0.1 M, maintained at 4° C. and 23° C., respectively; Samples 9 and 10 (controls): $CaCl_2$ 0.1 M, maintained at 4° C. and 23° C., respectively). The extraction time for Samples 1-10 is 24 hours. The spectra of two samples are also shown (Sample 11: glucose 0.1 M; Sample 12: $CaCl_2$ 0.1 M) extracted after maintaining the suspension for 5 hours at room temperature (23° C.). The extracts were diluted to perform the spectrophotometric measurements.

After that, the samples (biomass pellets) were suspended in 5 mL of extracting solution (Samples 1, 2 and 11 in glucose (monosaccharide) 0.1M, Samples 3-4 in fructose (monosaccharide) 0.1 M, Samples 5-6 in table sugar (sucrose, disaccharide) 0.1 M, Samples 7-8 in sorbitol (polyol) 0.1 M, Samples 9, 10 and 12 in CaCl₂ 0.1 M (control)) and extracted by applying the conditions (extraction temperature and time) reported in Table 18. At the end of the extraction period, the suspensions were centrifuged (30 min, 12000×g, 20° C.), the supernatant (extract) recovered; the content and purity of B-PE (FIG. 21 and Table 18) were determined by spectrophotometric analysis (see Ex. 6).

TABLE 18

% yield (Y) (mg/mg dry weight of the biomass) and purity of *P. cruentum* extracts obtained by means of the method of the invention.

| Sample | Extracting solution | t (hours)/ Extraction | T (° C.)/ Extraction | $Y_{B\text{-}PE}$ % | $P_{B\text{-}PE}$ |
|---|---|---|---|---|---|
| 1 | Glucose 0.1M | 24 | 4 | 4.21 | 2.63 |
| 2 | Glucose 0.1M | 24 | 23 | 4.63 | 2.10 |
| 3 | Fructose 0.1M | 24 | 4 | 4.28 | 2.72 |
| 4 | Fructose 0.1M | 24 | 23 | 4.47 | 2.14 |
| 5 | Sucrose 0.1M | 24 | 4 | 4.29 | 2.74 |
| 6 | Sucrose 0.1M | 24 | 23 | 4.34 | 2.12 |
| 7 | Sorbitol 0.1M | 24 | 4 | 4.24 | 2.71 |
| 8 | Sorbitol 0.1M | 24 | 23 | 4.39 | 2.08 |
| 9 | CaCl₂ 0.1M | 24 | 4 | 4.15 | 2.96 |
| 10 | CaCl₂ 0.1M | 24 | 23 | 4.15 | 2.42 |
| 11 | Glucose 0.1M | 5 | 23 | 3.73 | 2.08 |
| 12 | CaCl₂ 0.1M | 5 | 23 | 3.73 | 2.88 |

EX. 19: Extraction of Phycobiliproteins (Phycocyanin and Allophycocyanin) from a Fresh (Wet) Biomass of *A. platensis* (*Spirulina*): Use of Various Carbohydrates as Extracting Solutions An aliquot of *A. platensis* cell culture was filtered using a nylon filter (mesh size=21 μm), to separate the biomass from the culture medium. The biomass was recovered from the filter using a spatula and was suspended in a small volume of MilliQ ultrapure water in order to obtain a rather dense suspension.

2 mL of the suspension was filtered using a Whatman glass fibre filter (GF/C grade). The biomass was washed with MilliQ water on the same filter and the weight of the dry biomass was determined after drying at 105° C. for 5 and a half hours.

Extraction/purification process according to the invention: 8 aliquots of 5.7 mL were withdrawn from the biomass suspension. A volume of 3.3 mL of AS 3 M was added to each aliquot, so as to have a final volume of 9 mL of suspension in AS 1.1 M (cleaning solution).

Each suspension was submitted to an initial sonication cycle (2 min, power 100%, pulsation 1 s (i.e., continuous sonication), sonotrode S2, Hielscher Ultrasonic Processor UP200S, 200 W, 24 kHz) in an ice/water bath. After the first sonication cycle, the suspensions were kept in an ice/water bath for at least 1 minute and were then submitted to a second sonication cycle. The suspensions were then kept under stirring at room temperature (24° C.) at 250 rpm for 10 min by means of an orbital shaker, then centrifuged (15 min, 12000×g, 20° C.) and the supernatant removed.

The process of cleaning/cell lysis was repeated a second time.

Figure 22:
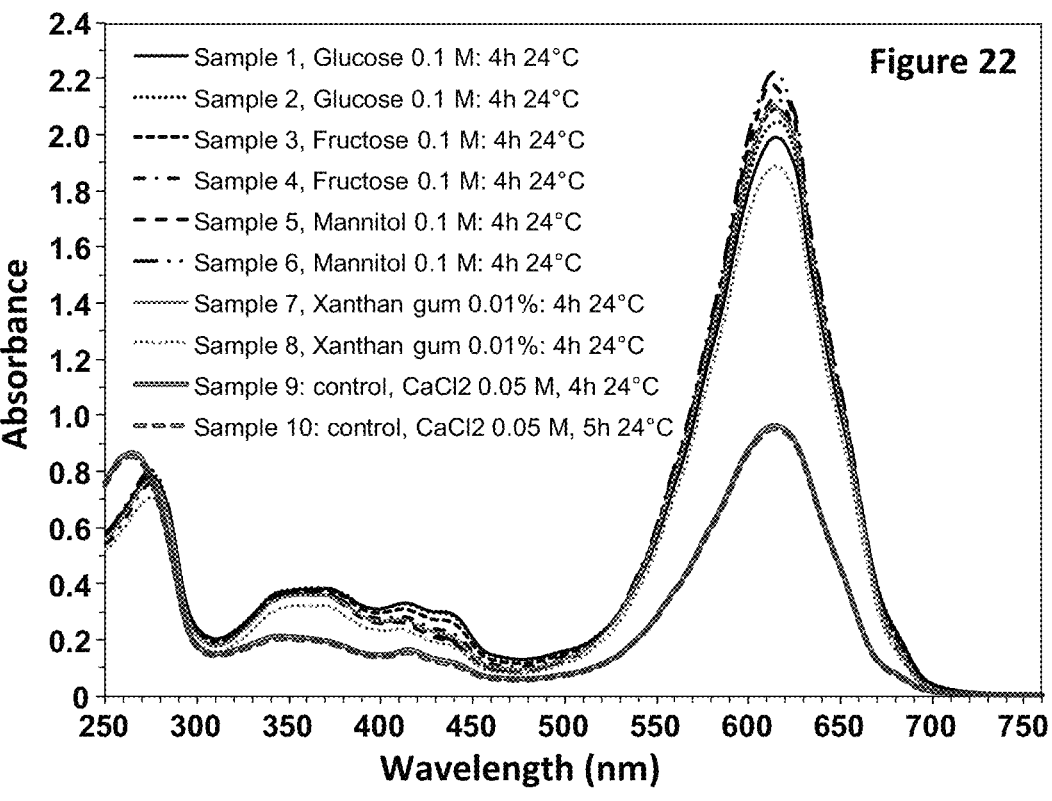
FIG. 22: Absorbance spectra of diluted solutions of *Spirulina* extracts obtained by applying the method of the invention, using different extracting solutions (Samples 1 and 2: glucose 0.1 M; Samples 3 and 4: fructose 0.1 M; Samples 5 and 6: mannitol 0.1 M; Samples 7 and 8: xanthan gum 0.01%). The spectra of two control extracts, obtained by sonicating two samples directly in the extracting solvent ($CaCl_2$ 0.05M) under conditions of low cell density and by keeping the suspension under stirring for 4 hours (Sample 9) or for 5 hours (Sample 10), are also shown. The extracts of Samples 1-8 were diluted to perform the spectrophotometric measurements.

After that, the samples (biomass pellets) were suspended in 3 mL of extracting solution (Samples 1-2 in glucose (monosaccharide) 0.1 M, Samples 3-4 in fructose (monosaccharide) 0.1 M, Samples 5-6 in mannitol (polyol) 0.1 M, Samples 7-8 in xanthan gum (complex carbohydrate, polysaccharide) 0.01%), stirred at room temperature (24° C.) at 250 rpm for 4 hours by means of an orbital shaker, centrifuged (30 min, 12000×g, 20° C.), the supernatant (extract) recovered, the phycobiliprotein content and PC purity (FIG. 22 and Table 19) determined by spectrophotometric analysis (see Ex. 1). The ratio of the volume of the extracting solution (expressed in mL) to the dry weight of the extracted biomass (expressed in g) is equal to 35.2.

Control extraction: two samples were prepared by diluting 0.5 mL of biomass suspension in 8.5 mL of CaCl₂ 0.05 M. (Samples 9 and 10). The two samples were submitted to a first sonication cycle (2 min, power 100%, pulsation 1 s (i.e. continuous sonication), sonotrode S2, Hielscher Ultrasonic Processor UP200S, 200 W, 24 kHz) in an ice/water bath. After the first sonication cycle, the samples were kept in an ice/water bath for at least 1 minute and were then submitted to a second sonication cycle. The samples were then kept under stirring at room temperature (24° C.) at 250 rpm by means of an orbital shaker, one for 4 hours (Sample 9) and the other one for 5 hours (Sample 10). Subsequently, the samples were centrifuged (30 min, 12000×g, 20° C.) and the supernatant (extract) recovered, the phycobiliprotein content and PC purity (FIG. 22 and Table 19) were determined by spectrophotometric analysis (see Ex. 1). The ratio of the volume of the extracting solution (expressed in mL) to the dry weight of the extracted biomass (expressed in g) is equal to 1204.

TABLE 19

% yield (Y) (mg/mg dry weight of the biomass) and purity of Spirulina extracts obtained by means of the method of the invention.

| Sample | Extracting solution | [PC + APC] (mg/mL) | $Y_{PC}$ % | $Y_{APC}$ % | $Y_{PC+APC}$ % | $P_{PC}$ |
|---|---|---|---|---|---|---|
| 1 | Glucose 0.1M | 5.3009 | 13.62 | 4.92 | 18.54 | 2.69 |
| 2 | Glucose 0.1M | 5.4389 | 14.06 | 5.08 | 19.15 | 2.74 |
| 3 | Fructose 0.1M | 5.5593 | 14.43 | 5.14 | 19.57 | 2.82 |
| 4 | Fructose 0.1M | 5.6592 | 14.26 | 5.00 | 19.26 | 2.96 |
| 5 | Mannitol 0.1M | 5.7578 | 13.93 | 4.86 | 18.79 | 2.92 |
| 6 | Mannitol 0.1M | 5.8850 | 14.22 | 4.84 | 19.06 | 2.93 |
| 7 | Xanthan gum 0.01% | 5.5712 | 14.28 | 5.00 | 19.28 | 2.89 |
| 8 | Xanthan gum 0.01% | 5.0149 | 13.49 | 4.75 | 18.24 | 2.84 |
| 9/contr | CaCl₂ 0.05M/4 h | 0.1864 | 16.80 | 5.27 | 22.07 | 1.41 |
| 10/contr | CaCl₂ 0.05M/5 h | 0.1836 | 16.70 | 5.16 | 21.86 | 1.43 |

EX. 20: Extraction of Phycobiliproteins (Phycocyanin and Allophycocyanin) from a Fresh (Wet) Biomass of *A. platensis* (*Spirulina*): Effect of the Concentration of Xanthan Gum (Polysaccharide) in the Extracting Solution An aliquot of *A. platensis* cell culture was filtered using a nylon filter (mesh size=21 µm), to separate the biomass from the culture medium. The biomass was recovered from the filter using a spatula and was suspended in a small volume of MilliQ ultrapure water in order to obtain a rather dense suspension.

Figure 23:
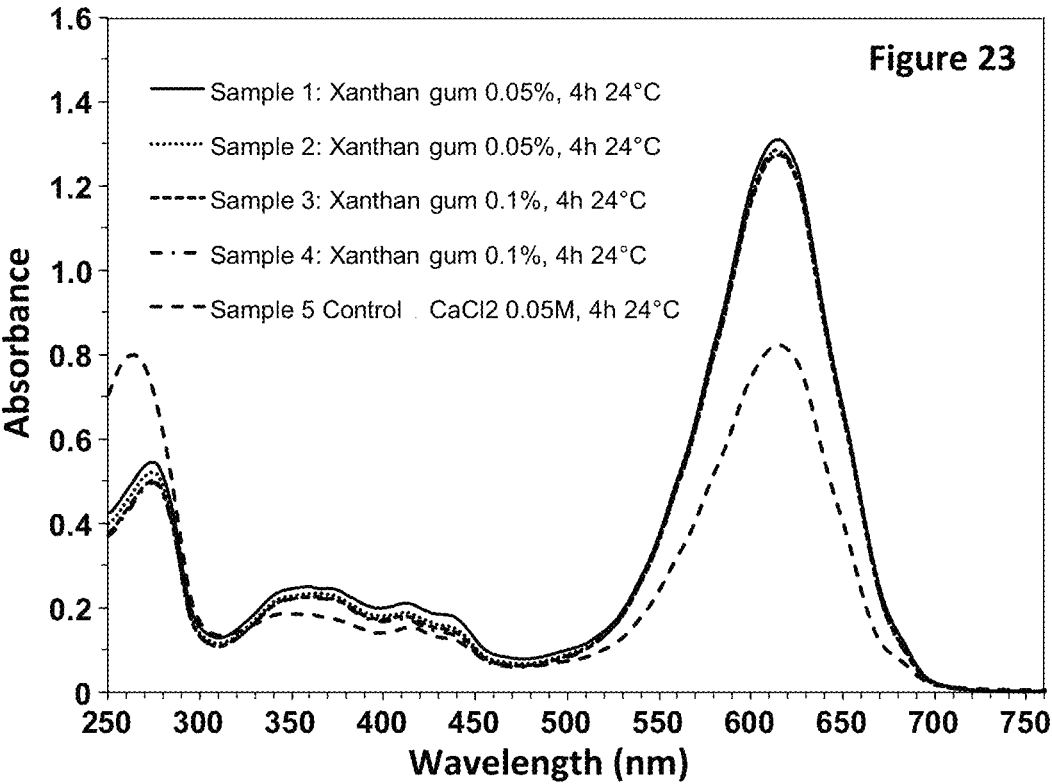
FIG. 23: Absorbance spectra of diluted solutions of *Spirulina* extracts obtained by applying the method of the invention, using extracting solutions of xanthan gum of different concentrations (Samples 1 and 2: xanthan gum 0.05%; Samples 3 and 4: xanthan gum 0.1%). The absorbance spectrum of a control extract obtained by sonicating the sample directly in the extracting solvent (Sample 5: $CaCl_2$ 0.05M) under low cell density conditions is also shown. The extracts of Samples 1-4 were diluted to perform the spectrophotometric measurements.

2 mL of the suspension was filtered using a Whatman glass fibre filter (GF/C grade). The biomass was washed UP200S, 200 W, 24 kHz) in an ice/water bath. After the first sonication cycle, the sample was kept in an ice/water bath for at least 1 minute and was then submitted to a second sonication cycle. The sample was then kept under stirring at room temperature (24° C.) at 250 rpm by means of an orbital shaker for 4 hours. Subsequently, the sample was centrifuged (30 min, 12000×g, 20° C.) and the supernatant (extract) recovered, the phycobiliprotein content and PC purity (FIG. 23 and Table 20) were determined by spectrophotometric analysis (see Ex. 1). The ratio of the volume of the extracting solution (expressed in mL) to the dry weight of the extracted biomass (expressed in g) is equal to 1300.

TABLE 20

% yield (Y) (mg/mg dry weight of the biomass) and purity of Spirulina extracts obtained by means of the method of the invention.

| Sample | Extracting solution | [PC + APC] (mg/mL) | $Y_{PC}$ % | $Y_{APC}$ % | $Y_{PC+APC}$ % | $P_{PC}$ |
|---|---|---|---|---|---|---|
| 1 | Xanthan gum 0.05% | 3.5096 | 12.95 | 4.84 | 17.78 | 2.58 |
| 2 | Xanthan gum 0.05% | 3.4362 | 12.68 | 4.74 | 17.41 | 2.65 |
| 3 | Xanthan gum 0.1% | 3.4149 | 12.72 | 4.75 | 17.48 | 2.73 |
| 4 | Xanthan gum 0.1% | 3.4405 | 12.46 | 4.73 | 17.19 | 2.77 |
| 5/contr | CaCl$_2$ 0.05M | 0.1596 | 15.51 | 5.00 | 20.51 | 1.36 | with MilliQ water on the same filter and the weight of the dry biomass was determined after drying at 105° C. for 5 hours.

Extraction/purification process according to the invention: 4 aliquots of 5.7 mL were withdrawn from the biomass suspension. A volume of 3.3 mL of AS 3 M was added to each aliquot, so as to have a final volume of 9 mL of suspension in AS 1.1 M (cleaning solution).

Each suspension was submitted to an initial sonication cycle (2 min, power 100%, pulsation 1 s (i.e., continuous sonication), sonotrode S2, Hielscher Ultrasonic Processor UP200S, 200 W, 24 kHz) in an ice/water bath. After the first sonication cycle, the suspensions were kept in an ice/water bath for at least 1 minute and were then submitted to a second sonication cycle. The suspensions were then kept under stirring at room temperature (24° C.) at 250 rpm for 10 min by means of an orbital shaker, then centrifuged (15 min, 12000×g, 20° C.) and the supernatant removed.

The process of cleaning/cell lysis was repeated a second time.

After that, the samples (biomass pellets) were suspended in 4 mL of extracting solution (Samples 1-2 in Hanthan gum 0.05%, Samples 3-4 in Hanthan gum 0.1%), stirred at room temperature (24° C.) at 250 rpm for 4 hours by means of an orbital shaker, centrifuged (30 min, 12000×g, 20° C.), the supernatant (extract) recovered, the phycobiliprotein content and PC purity (FIG. 23 and Table 20) determined by spectrophotometric analysis (see Ex. 1). The ratio of the volume of the extracting solution (expressed in mL) to the dry weight of the extracted biomass (expressed in g) is equal to 50.7.

Control extraction: a sample was prepared by diluting 0.5 mL of biomass suspension in 8.5 mL of CaCl$_2$ 0.05M (Sample 5). The sample was submitted to a first sonication cycle (2 min, power 100%, pulsation 1 s (i.e. continuous sonication), sonotrode S2, Hielscher Ultrasonic Processor EX. 21: Extraction of Phycobiliproteins (Phycocyanin and Allophycocyanin) from a Fresh (Wet) Biomass of *A. platensis* (*Spirulina*): Use of Dextran and Dextrin as Extracting Solutions and Effect of Dextran Concentration in the Extracting Solution An aliquot of *A. platensis* cell culture was filtered using a nylon filter (mesh size=21 µm), to separate the biomass from the culture medium. The biomass was recovered from the filter using a spatula and was suspended in a small volume of MilliQ ultrapure water in order to obtain a rather dense suspension.

1 mL of the suspension was filtered using a Whatman glass fibre filter (GF/C grade). The biomass was washed with MilliQ water on the same filter and the weight of the dry biomass was determined after drying at 105° C. for 5 hours.

Extraction/purification process according to the invention: 4 aliquots of 5.7 mL were withdrawn from the biomass suspension. A volume of 3.3 mL of AS 3 M was added to each aliquot, so as to have a final volume of 9 mL of suspension in AS 1.1 M (cleaning solution). Each suspension was submitted to an initial sonication cycle (2 min, power 100%, pulsation 1 s (i.e., continuous sonication), sonotrode S2, Hielscher Ultrasonic Processor UP200S, 200 W, 24 kHz) in an ice/water bath. After the first sonication cycle, the suspensions were kept in an ice/water bath for at least 1 minute and were then submitted to a second sonication cycle. The suspensions were then kept under stirring at room temperature (22.5° C.) at 200 rpm for 10 min by means of an orbital shaker, then centrifuged (15 min, 12000×g, 20° C.) and the supernatant removed. The cleaning/cell lysis process was repeated a second time, using a volume of cleaning solution (AS 1.1 M) equal to 11 mL. The ratio of the volume of the cleaning solution (expressed in mL) to the dry weight of the extracted biomass (expressed in g) is equal to 54.0 in the first cleaning cycle and 66.0 in the second cycle.

Afterwards, the samples (biomass pellets) were suspended in 6 mL of extracting solution (Sample 1: dextran 6000 30%, Sample: 2 dextran 6000 10%, Sample 3: dextran 6000 1%, Sample 4: dextrin 5%), stirred at room temperature (22.5° C.) at 200 rpm for 4 hours by means of an orbital shaker, centrifuged (30 min, 12000×g, 20° C.), the supernatant (extract) recovered, the phycobiliprotein content and PC purity (FIG. 24 and Table 21) determined by spectrophotometric analysis (see Es 1). The ratio of the volume of the extracting solution (expressed in mL) to the dry weight of the extracted biomass (expressed in g) is equal to 36.0.

TABLE 21

% yield (Y) (mg/mg dry weight of the biomass) and purity of Spirulina extracts obtained by means of the method of the invention.

| Sample | Extracting solution | [PC + APC] (mg/mL) | $Y_{PC}$ % | $Y_{APC}$ % | $Y_{PC+APC}$ % | $P_{PC}$ |
|--------|---------------------|--------------------|------------|-------------|----------------|----------|
| 1 | Dextran 6000 30% | 0.4622 | 1.20 | 0.51 | 1.71 | 0.30 |
| 2 | Dextran 6000 10% | 5.2084 | 13.96 | 4.82 | 18.78 | 2.04 |
| 3 | Dextran 6000 1% | 5.7328 | 15.54 | 4.78 | 20.32 | 2.76 |
| 4 | Dextrin 5% | 4.2738 | 10.44 | 3.94 | 14.38 | 2.93 |

The invention claimed is:

1. A method for extracting from cyanobacterial and/or algal biomasses phycobiliproteins having a purity degree≥2.0, comprising the steps of I) arranging a cyanobacterial and/or algal biomass;

II) cleaning the cyanobacterial and/or algal biomass, such cleaning step comprising the sub-steps of IIa) submitting the cyanobacterial and/or algal biomass to cell lysis by ultrasonication, said cyanobacterial and/or algal biomass being suspended in an aqueous cleaning solution of ammonium sulphate having a concentration between 0.4 and 2.0 M, to obtain a biomass lysed suspension;

IIb) separating from the suspension of the lysed biomass the cleaning solution and isolating the precipitate of the lysed biomass, such precipitate being a cleaned sample of the biomass wherein the phycobiliproteins are trapped in the lysed cells of the cyanobacterial and/or algal biomass;

III) extracting the phycobiliproteins from the biomass cleaned sample, said extraction step comprising the sub-steps of IIIa) suspending the biomass cleaned sample in an extracting solution selected from water and aqueous solutions, to obtain a suspension of the biomass cleaned sample;

IIIb) separating from the suspension of the biomass cleaned sample the extracting solution and isolating the supernatant, to obtain a crude extract of phycobiliproteins.

2. The method according to claim 1, wherein the cyanobacterial and/or algal biomass comprises *Arthrospira platensis (Spirulina)*, or *Porphyridium cruentum*, or combinations thereof.

3. The method according to claim 1, wherein the cleaning solution and the cyanobacterial and/or algal biomass are combined in a volume/weight ratio of the dry biomass (ml/g) between 10:1 and 1000:1.

4. The method according to claim 1, wherein the extracting aqueous solutions are selected from inorganic salt aqueous solutions, buffer aqueous solutions, carbohydrates aqueous solutions and polyol aqueous solutions.

5. The method according to claim 4, wherein the inorganic salts are selected from sodium chloride and calcium chloride.

6. The method according to claim 4, wherein the buffers are selected from the group consisting of citrate salts, acetate salts and phosphate salts.

7. The method according to claim 4, wherein the carbohydrates are selected from the group consisting of monosaccharides, disaccharides and polysaccharides.

8. The method according to claim 4, wherein the polyols are selected from the group consisting of sorbitol, mannitol and xylitol.

9. The method according to claim 1, wherein the extracting solution and the biomass are combined in a volume (ml)/weight ratio of the dry biomass (g) between 20 and 365.

10. The method according to claim 1, wherein the sub-step IIb and sub-step IIIb of separating comprise independently a sub-step of leaving the suspension, with or without stirring, after separation, at a temperature between 4° C. and 35° C.

11. The method according to claim 1, comprising a further step IV) of freeze-drying the phycobiliprotein extract.

12. The method according to claim 1, wherein the step II of cleaning the biomass is performed twice.

13. A process for purifying phycobiliproteins from cyanobacterial and/or algal biomasses comprising the following steps:

Pi) extracting from cyanobacterial and/or algal biomasses phycobiliproteins, by performing the method according to claim 1 to obtain a raw extract of further purifiable phycobiliproteins, so as to obtain a raw extract of phycobiliproteins having a purity (P) degree≥2.0;

Pii) performing at least one purification cycle of the raw extract through the passage of a saline aqueous solution of said raw extract over a hydrophilic porous membrane having a low protein binding capacity, wherein said aqueous saline solution of said raw extract of phycobiliproteins is an aqueous solution of a salt S with a concentration [S]1 capable of inducing selective and reversible binding of the phycobiliproteins to said membrane;

Piii) desorbing the retentate bound to said membrane by washing with a solvent selected from the group consisting of water, an aqueous solution of said salt S at a concentration [S]2<[S]1, and an aqueous solution of a salt S' which is a stronger chaotropic agent than said salt S, wherein the phycobiliproteins resulting from the purification process have an analytic purity (P) degree higher than 4.0.

14. A method for extracting from cyanobacterial and/or algal biomasses phycobiliproteins having a purity degree≥2.0, comprising the steps of I) arranging a cyanobacterial and/or algal biomass;

II) cleaning the cyanobacterial and/or algal biomass, such cleaning step comprising the sub-steps of IIa) submitting the cyanobacterial and/or algal biomass to cell lysis by ultrasonication, said cyanobacterial and/or algal biomass being suspended in an aqueous cleaning solution of ammonium sulphate having a concentration between 0.4 and 2.0 M, to obtain a biomass lysed suspension;

IIb) separating from the suspension of the lysed biomass the cleaning solution and isolating the precipitate of the lysed biomass, such precipitate being a cleaned sample of the biomass wherein the phycobiliproteins are trapped in the lysed cells of the cyanobacterial and/or algal biomass;

III) extracting the phycobiliproteins from the biomass cleaned sample, said extraction step comprising the sub-steps of IIIa) suspending the biomass cleaned sample in an extracting solution selected from water and aqueous solutions, to obtain a suspension of the biomass cleaned sample, wherein the extraction aqueous solutions are selected from inorganic salt aqueous solutions, buffer aqueous solutions, carbohydrates aqueous solutions and polyol aqueous solutions, and wherein the inorganic salts are selected from sodium chloride and calcium chloride;

IIIb) separating from the suspension of the biomass cleaned sample the extracting solution and isolating the supernatant, to obtain a crude extract of phycobiliproteins.

\* \* \* \* \*